(12) United States Patent
Sansoucy et al.

(10) Patent No.: US 7,815,046 B2
(45) Date of Patent: Oct. 19, 2010

(54) SHARPS DISPENSING AND DISPOSAL SYSTEM

(75) Inventors: Michael Sansoucy, Wrentham, MA (US); M. Brian Finnestad, Franklin, MA (US)

(73) Assignee: Tyco Healthcare Group LP, Mansfield, MA (US)

( * ) Notice: Subject to any disclaimer, the term of this patent is extended or adjusted under 35 U.S.C. 154(b) by 164 days.

(21) Appl. No.: 11/933,727

(22) Filed: Nov. 1, 2007

(65) Prior Publication Data

US 2009/0114667 A1 May 7, 2009

(51) Int. Cl.
B65D 83/10 (2006.01)
A47F 1/00 (2006.01)

(52) U.S. Cl. ............. 206/366; 220/908; 221/102

(58) Field of Classification Search ......... 206/364–366, 206/370; 220/908; 221/101–102
See application file for complete search history.

(56) References Cited

U.S. PATENT DOCUMENTS

| | | | |
|---|---|---|---|
| 516,961 A | 3/1894 | Boylan | |
| 3,889,804 A | 6/1975 | Ravich | |
| 4,588,093 A | 5/1986 | Field | |
| 4,809,850 A | 3/1989 | Laible et al. | |
| 5,084,028 A | 1/1992 | Kennedy et al. | |
| 5,097,950 A | 3/1992 | Weiss et al. | |
| 5,143,210 A | 9/1992 | Warwick et al. | |
| 5,152,394 A | 10/1992 | Hughes | |
| 5,245,117 A * | 9/1993 | Withers et al. ............. | 206/366 |
| 5,251,783 A | 10/1993 | Gringer | |
| 5,361,902 A * | 11/1994 | Abidin et al. ............. | 206/370 |
| 5,405,043 A | 4/1995 | Meloney | |
| 5,494,158 A | 2/1996 | Erickson | |
| 5,662,235 A | 9/1997 | Nieto | |
| 5,706,942 A | 1/1998 | Vila et al. | |
| 5,740,909 A | 4/1998 | Nazare et al. | |

(Continued)

FOREIGN PATENT DOCUMENTS

DE 538682 C 11/1931

(Continued)

OTHER PUBLICATIONS

International Search Report dated Sep. 1, 2006, application No. PCT/US2006/016736.

(Continued)

*Primary Examiner*—Bryon P Gehman
(74) *Attorney, Agent, or Firm*—Lisa E. Winsor, Esq.

(57) ABSTRACT

A sharps dispensing and disposal system includes a sharps dispensing container and a sharps disposal container within the sharps dispensing container. In one embodiment, the sharps disposal container is mounted at least partially within the sharps dispensing container, with a chamber surrounding at least a portion of the sharps disposal container. In another embodiment, a sharps dispensing and disposal system includes a sharps disposal container having an inner wall and an inlet for depositing used sharps into the sharps disposal container. The sharps dispensing container includes an outer wall that surrounds at least a portion of the sharps disposal container and forms a buffer zone. In another embodiment, a sharps dispensing and disposal system includes at least one elastic support member that elastically suspends a sharps disposal container in the interior of a sharps dispensing container. A cover detachably couples the sharps disposal container with the sharps dispensing container.

8 Claims, 24 Drawing Sheets

U.S. PATENT DOCUMENTS

| | | |
|---|---|---|
| 5,878,899 A | 3/1999 | Manganiello et al. |
| 6,685,017 B2 | 2/2004 | Erickson |
| 6,702,147 B2 | 3/2004 | Ashford |
| 6,923,319 B1 * | 8/2005 | Erickson et al. ............. 206/366 |
| 7,513,363 B2 * | 4/2009 | Brown et al. ................ 206/366 |
| 7,556,149 B2 * | 7/2009 | Erickson et al. ............. 206/366 |
| 2002/0190073 A1 | 12/2002 | Hewett |
| 2003/0132129 A1 | 7/2003 | Erickson |
| 2003/0226851 A1 | 12/2003 | Antebi |
| 2003/0226879 A1 | 12/2003 | Auclair et al. |
| 2006/0243635 A1 * | 11/2006 | Sullivan et al. ............. 206/571 |

FOREIGN PATENT DOCUMENTS

| | | |
|---|---|---|
| DE | 9214287 U1 | 1/1993 |
| EP | 1449491 A | 8/2004 |
| GB | 2275673 A | 9/1994 |
| WO | WO 9101920 A2 | 2/1991 |
| WO | WO 2005/120610 | 12/2005 |

OTHER PUBLICATIONS

International Search Report corresponding to Application No. PCT/US2006/016320 dated Sep. 29, 2006.

* cited by examiner

US 7,815,046 B2

SHARPS DISPENSING AND DISPOSAL SYSTEM

FIELD OF THE INVENTION

The present invention relates generally to medical waste containers and more specifically to containers for the safe disposal of sharps.

BACKGROUND OF THE INVENTION

A variety of containers have been developed for the collection and storage of needle syringes and other sharps. A primary function of the containers is to provide a rigid enclosure that protects individuals from becoming injured by an exposed sharps. This function is especially significant in the handling of used sharps during disposal. Used sharps that are not properly contained pose a risk of serious injury to personnel who handle the used sharps. Accidental contact with a used needle can result in the transmission of various pathogens, including human immunodeficiency virus (HIV). In view of the risks associated with exposed sharps, sharps containers provide a safe way to store sharps during transport and disposal.

SUMMARY OF THE INVENTION

A sharps disposal container is combined with a sharps dispensing container in several embodiments of the invention. In a first embodiment, a sharps dispensing and disposal system includes a sharps dispensing container having an outer wall and a sharps disposal container having an inner wall. The sharps disposal container is mounted at least partially within the sharps dispensing container. A chamber surrounds at least a portion of the sharps disposal container.

In a second embodiment of the invention, a sharps dispensing and disposal system includes a sharps disposal container having an inner wall and an inlet for depositing used sharps into the sharps disposal container. A sharps dispensing container includes an outer wall that surrounds at least a portion of the sharps disposal container. The outer wall forms a buffer zone extending between the inner wall and the outer wall.

In a third embodiment of the invention, a sharps dispensing and disposal system includes a sharps dispensing container having an outer wall forming a hollow interior and a sharps disposal container. The sharps disposal container has at least one elastic support member that elastically suspends the sharps disposal container in the hollow interior of the sharps dispensing container. A cover detachably couples the sharps disposal container with the sharps dispensing container in the elastically suspended condition.

BRIEF DESCRIPTION OF THE DRAWINGS

The foregoing summary and the following description will be better understood in conjunction with the drawing figures, of which.

DETAILED DESCRIPTION OF PREFERRED EMBODIMENTS OF THE INVENTION

Figure 1:
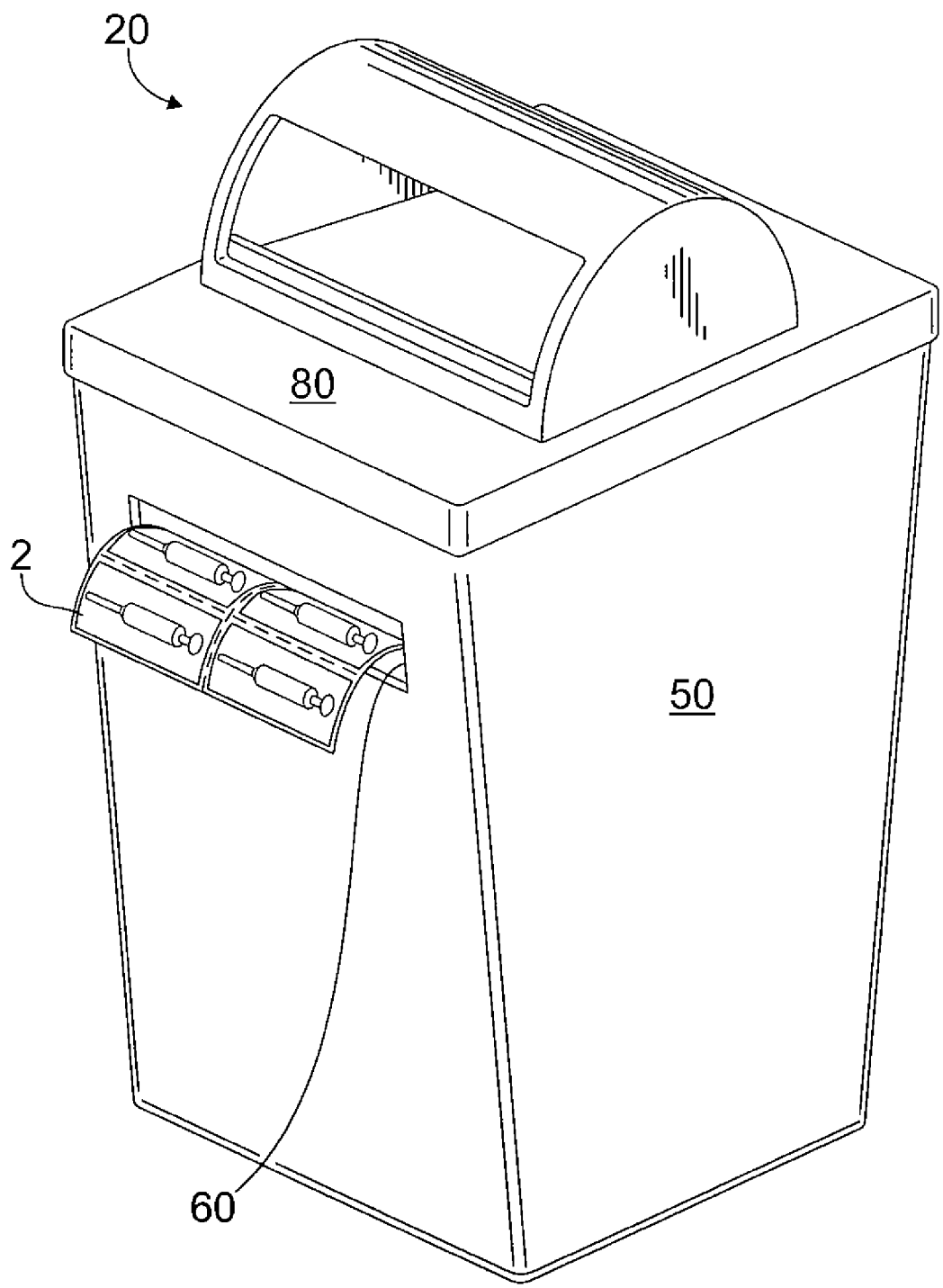
FIG. 1 is a perspective view of a first exemplary embodiment of a sharps dispensing and disposal system in accordance with the invention.
Figure 2:
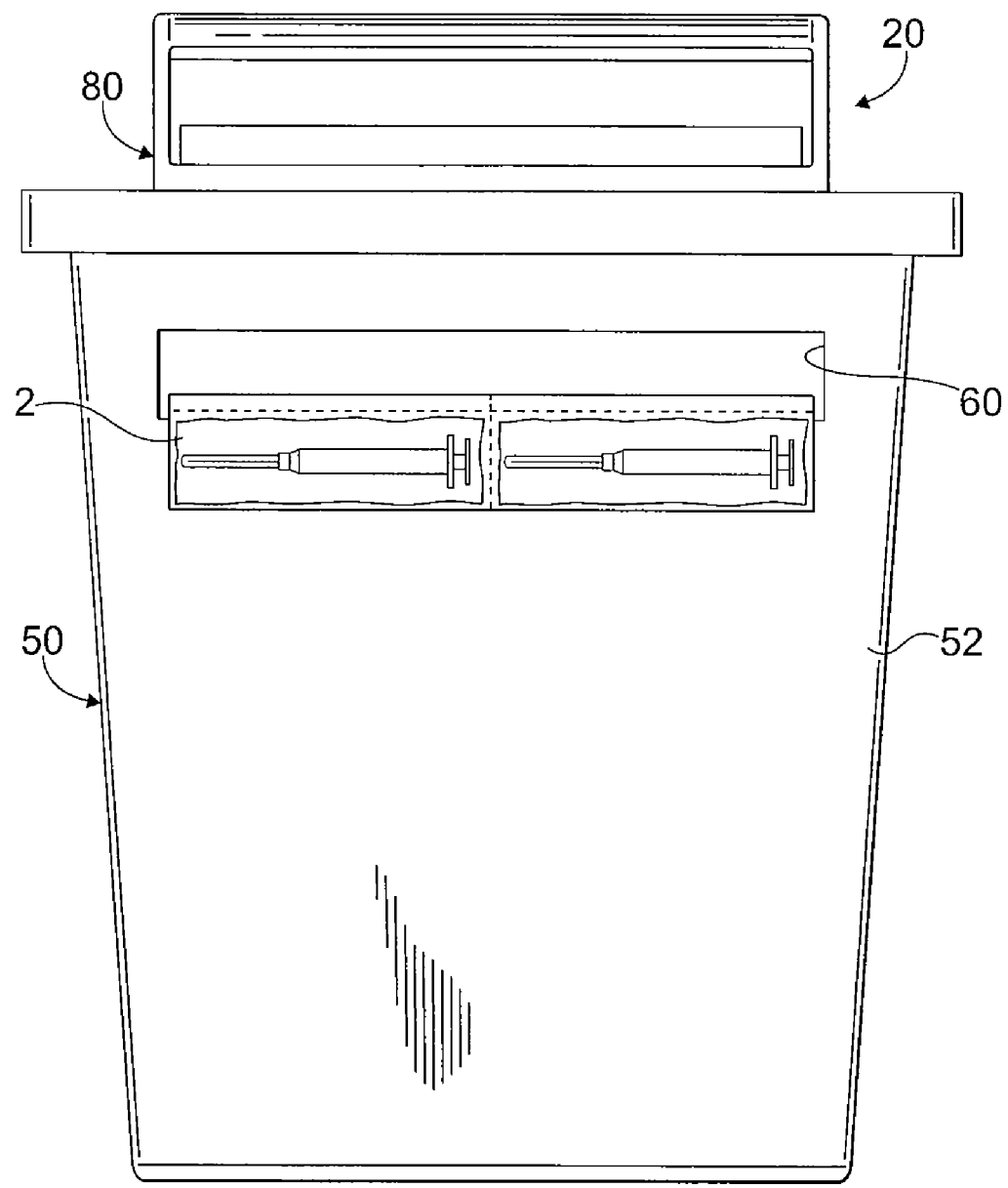
FIG. 2 is a front elevation view of the sharps dispensing and disposal system of FIG. 1.
Figure 3:
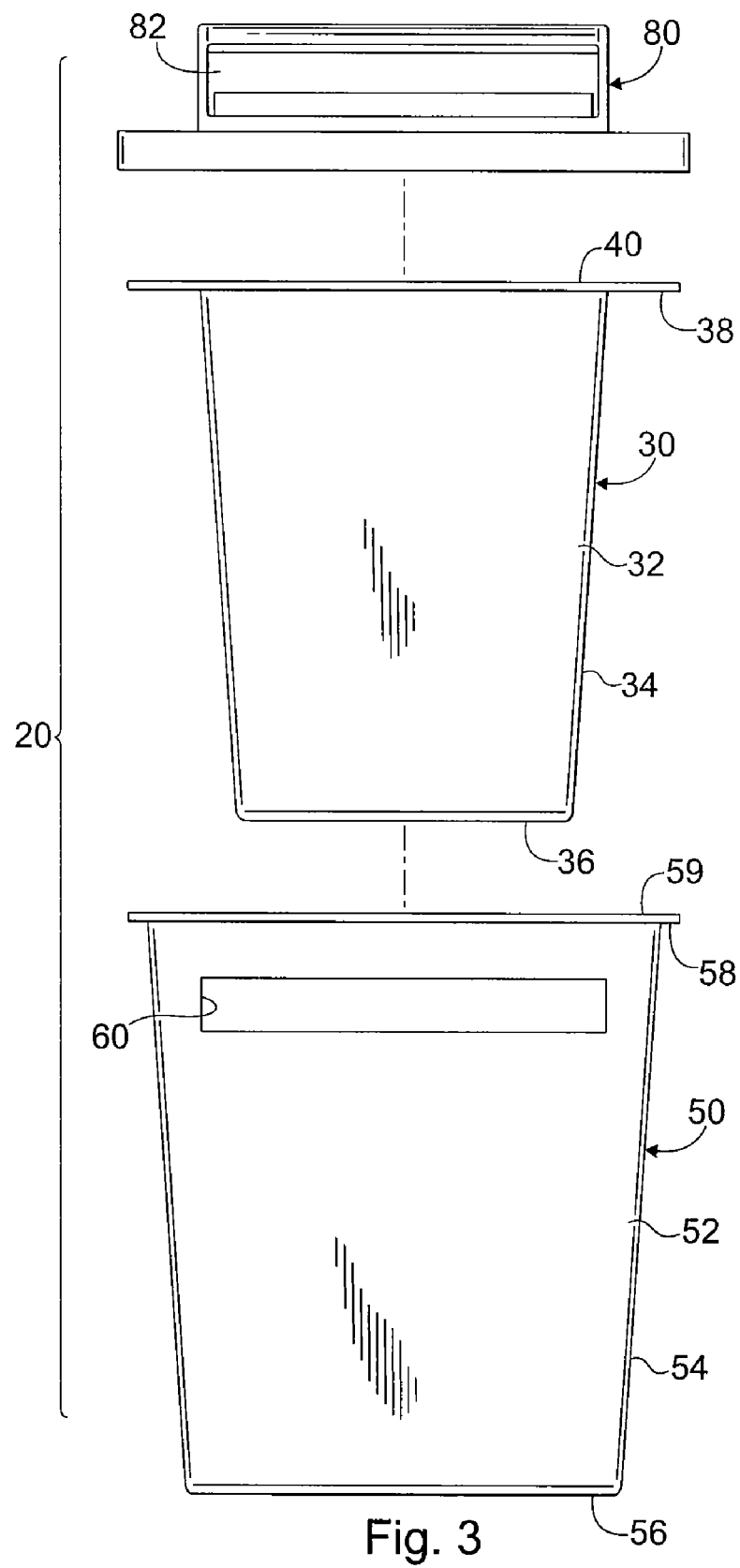
FIG. 3 is an exploded front elevation view showing disassembled components of the sharps dispensing and disposal system of FIG. 1.
Figure 4:
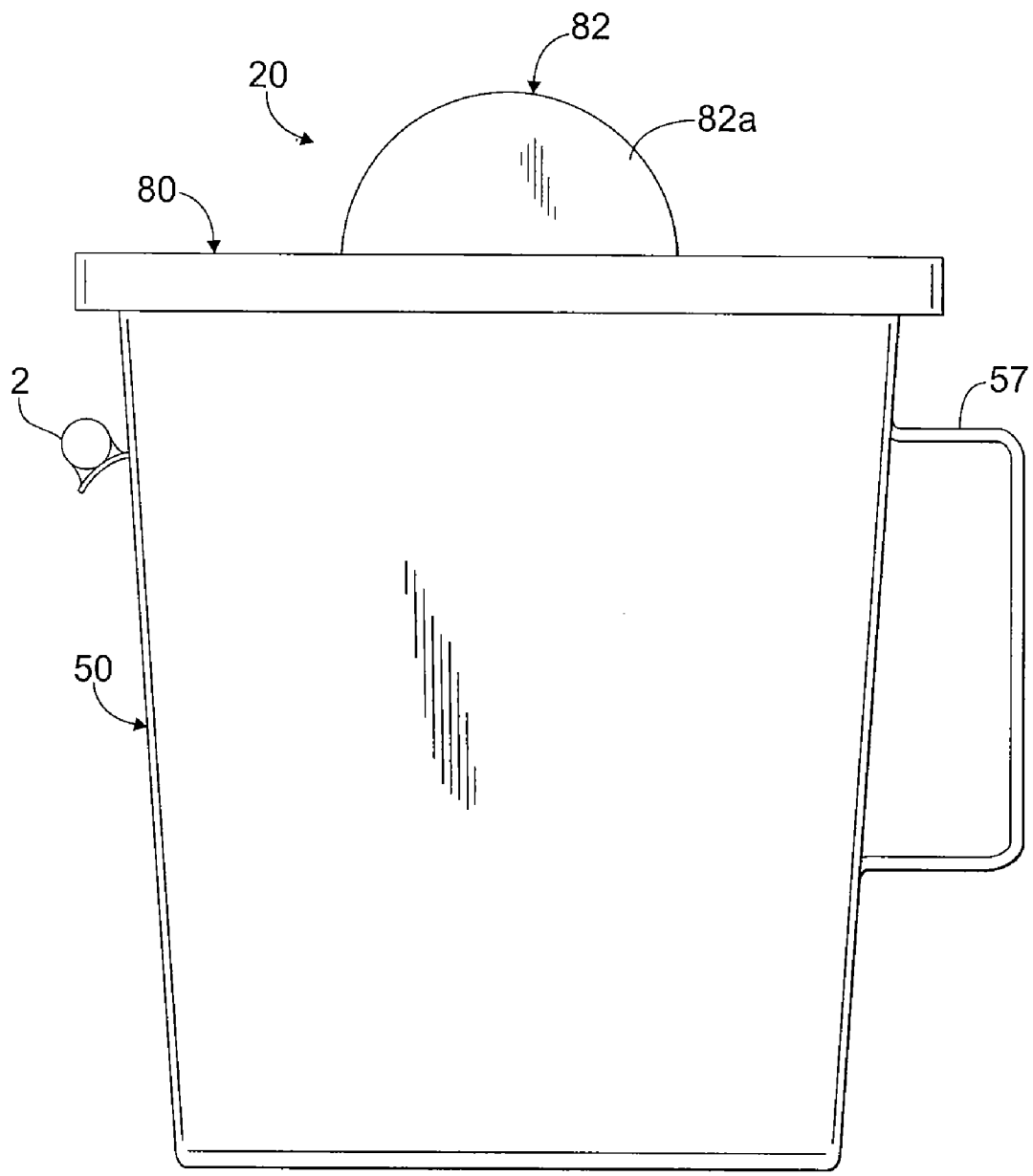
FIG. 4 is a side elevation view of the sharps dispensing and disposal system of FIG. 1.

Referring to the drawing figures generally, and FIGS. 1-5 in particular, a sharps dispensing and disposal system 20 according to a first exemplary embodiment of the invention is shown. System 20 provides an improved safety disposal apparatus for contaminated sharps that addresses multiple needs in one compact unit. An inner container in system 20 provides a puncture resistant enclosure for discarded sharps. An outer portion of system 20 provides a dispensing apparatus for unused or sterile sharps. Contaminated sharps are confined within a dual-wall construction formed by suspending the inner container inside the outer container. The dual-wall construction substantially prevents contaminated needles from puncturing through the container walls by providing two layers of obstruction. The inner container protects discarded sharps from being subject to external shock forces exerted on the outer container. The dual-wall construction and internal suspension of the inner container substantially decrease the potential for sharps puncturing through container system and releasing liquid biohazards in the event that the container system is dropped.

System 20 includes a sharps disposal container 30 mounted in a stacked arrangement inside a sharps dispensing container 50. Disposal container 30 and dispensing container 50 are interconnected by a lid or cover 80 that attaches to the top portions of the containers. Cover 80 fixes disposal container 30 in a suspended condition inside dispensing container 50. In this arrangement, disposal container 30 and dispensing container 50 form a double walled containment system. Disposal container 30, dispensing container 50 and lid 80 are all preferably formed of puncture resistant material(s) suitable for the safe disposal and storage of sharps. In addition, for reasons that will be explained further below, the components are preferably formed of a resilient flexible material. Polypropylene provides one example of a material that can provide suitable puncture resistance and flexibility.

Disposal container 30 provides an inner wall 32 when system 20 is assembled. Inner wall 32 may have a plurality of configurations or shapes, but preferably includes a generally rectangular top cross-section and a generally trapezoidal side cross-section. In the drawing figures, inner wall 32 includes a plurality of sidewalls 34 and a bottom wall 36. Sidewalls 34 extend away from bottom wall 36 and terminate to form a top opening 40. A flange 38 extends outwardly from top opening 40.

Dispensing container 50 provides an outer wall 52 for system 20 when the system is assembled. Outer wall 52, like inner wall 32, may have a plurality of configurations or shapes, but preferably has a generally rectangular top cross-section and a generally trapezoidal side cross-section. In the drawing figures, outer wall 52 includes a plurality of sidewalls 54 and a bottom wall 56. Sidewalls 54 extend away from bottom wall 56 and terminate to form a top opening 59. Top opening 59 is surrounded by a substantially flat rim 58 that extends outwardly from top opening 59.

Dispensing container 50 is adapted to receive disposal container 30 in a stacked arrangement. Rim 58 of dispensing container 50 includes a support surface or shelf 58a that extends on all four sides of the dispensing container. Shelf 58a supports flange 38 of disposal container 30 in the assembled condition. Flange 38 has outer dimensions that are greater than the dimensions of top opening 59 on dispensing container 50. In this configuration, flange 38 overlaps shelf 58a on all four sides of dispensing container 50 when disposal container 30 is stacked inside dispensing container 50.

Figure 5:
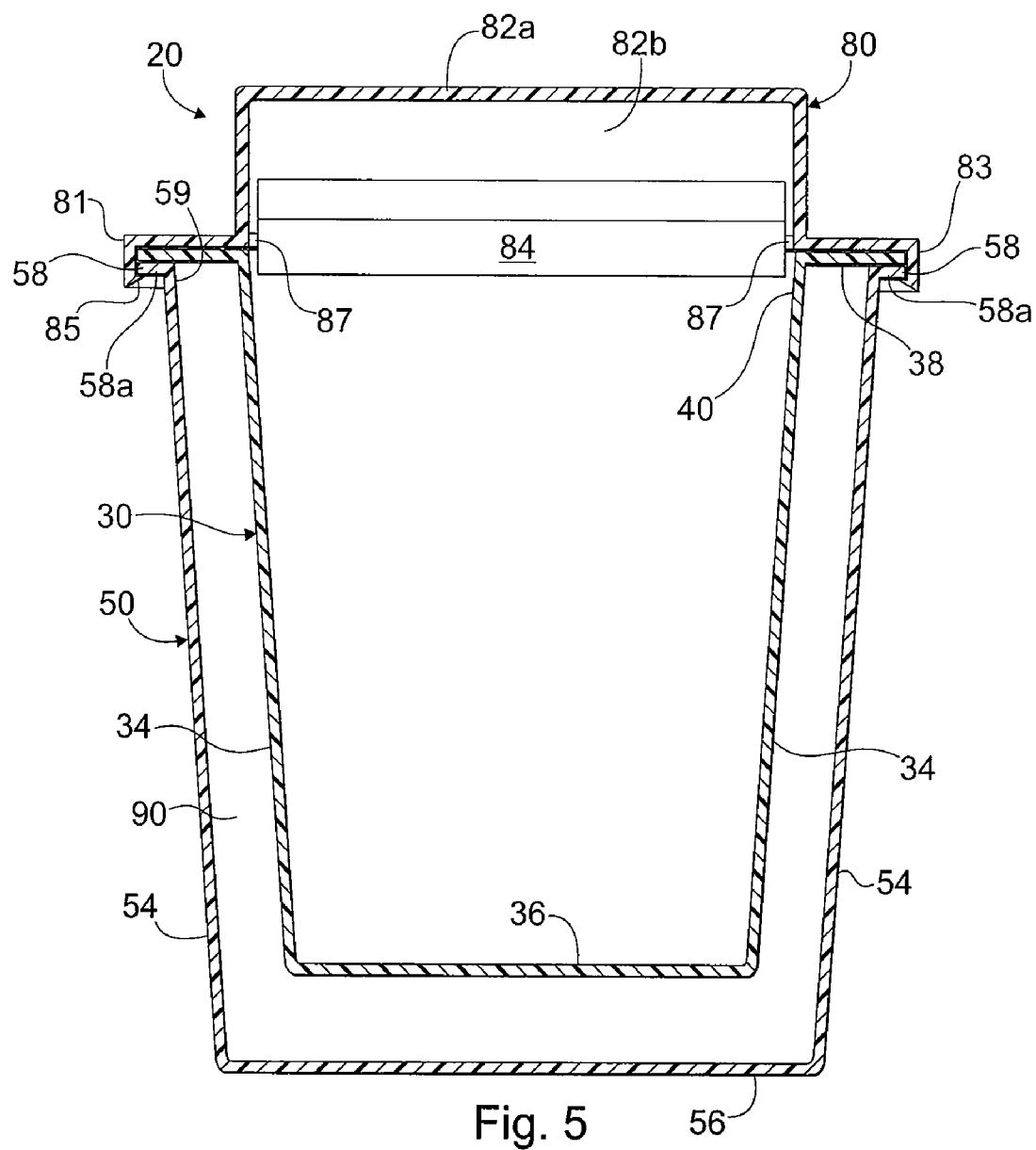
FIG. 5 is a front cross sectional view of the sharps dispensing and disposal system of FIG. 1, showing the system under a static condition.
Figure 5A:
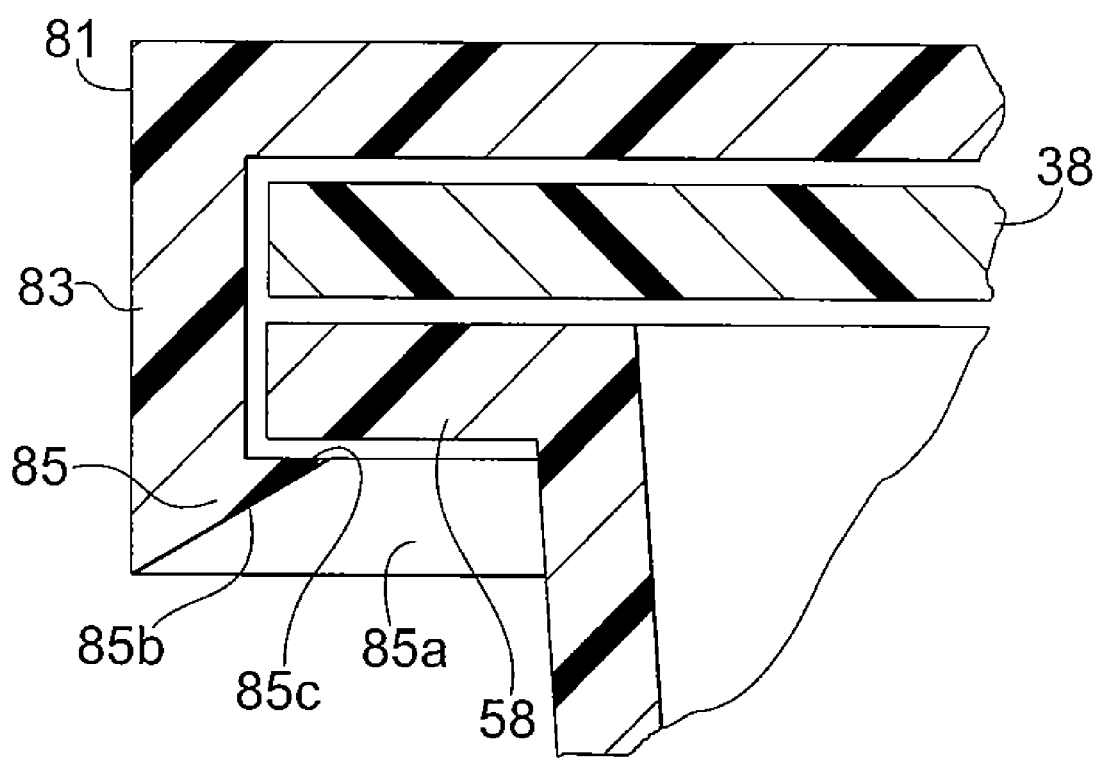
FIG. 5A is an enlarged front cross sectional view of a section of the sharps dispensing and disposal system shown in FIG. 5.

In a preferred embodiment, the cover securely connects onto the containers and requires minimal assembly. In FIG. 5, cover 80 is formed of polypropylene and includes a generally rectangular skirt 81 that fits over rim 58 of dispensing container 50. Skirt 81 forms a rim 83 that connects over rim 58 of dispensing container 50 and flange 38 of disposal container 30. Rim 83 includes a tabbed edge 85 that fits around the underside of rim 58 on dispensing container 50. Skirt 81 straddles both flange 38 and rim 58, with the flange and rim clamped between tabbed edge 85 and a top face 89 of lid 80. Tabbed edge 85 forms an opening 85a on the underside of cover 80. Opening 85a has dimensions that are slightly less than the dimensions of flange 38 and rim 58. A ramped face 85b on tabbed edge 85 assists in spreading the tabbed edge outwardly to fit around flange 38 and rim 58 when cover 80 is pressed downwardly onto the containers. A flat face 85c that extends generally normal to rim 83 further assists in detachably securing tabbed edge 85 around the respective perimeters of flange 38 and rim 58.

The sharps dispensing and disposal system is preferably compatible with a variety of lid configurations. Cover 80, for example, includes a drop inlet 82 for depositing used sharps in disposal container 30. Drop inlet 82 includes a hood 82a surrounding a chute 82b that conveys sharps into disposal container 30 by gravity. A pivoting door 84 forms a surface for receiving sharps in a generally horizontal orientation. Door 84 is pivotally mounted inside hood 82a by a pair pins 87. Each pin 87 partially extends into door 84, and fits into a pivot hole inside hood 82a. In this arrangement, door 84 is configured to tilt in response to a sharps device being placed onto the door, for example at a position offset from the door's center of gravity, at which time the door pivots and drops the sharps into the disposal container. A small ledge 84a on one end of the door 84 initially prevents the sharps from rolling off the door until the sharps is tilted to a position where the sharps can fall into the disposal container.

Figure 7:
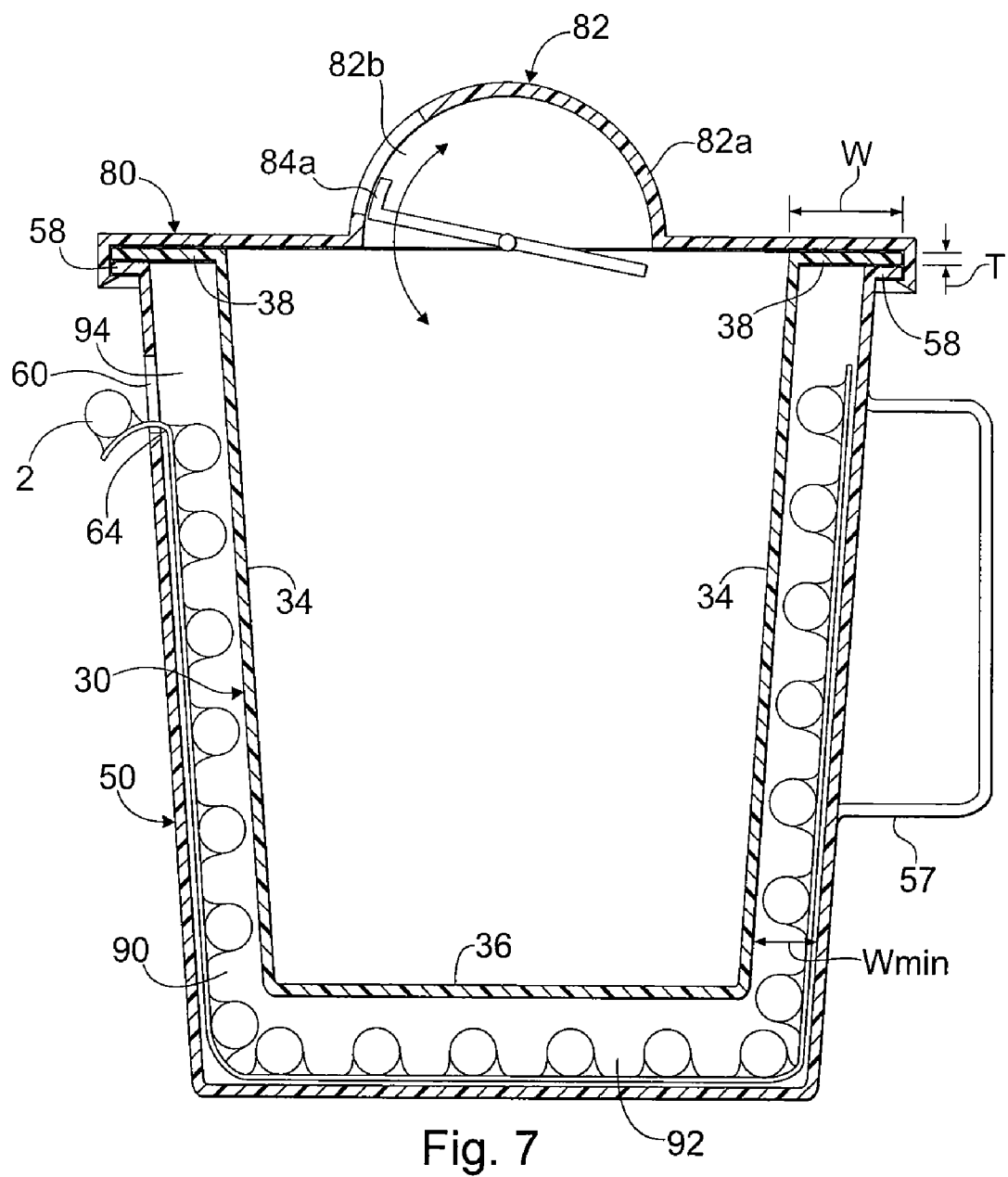
FIG. 7 is a side cross sectional view of the sharps dispensing and disposal system of FIG. 1.
Figure 8:
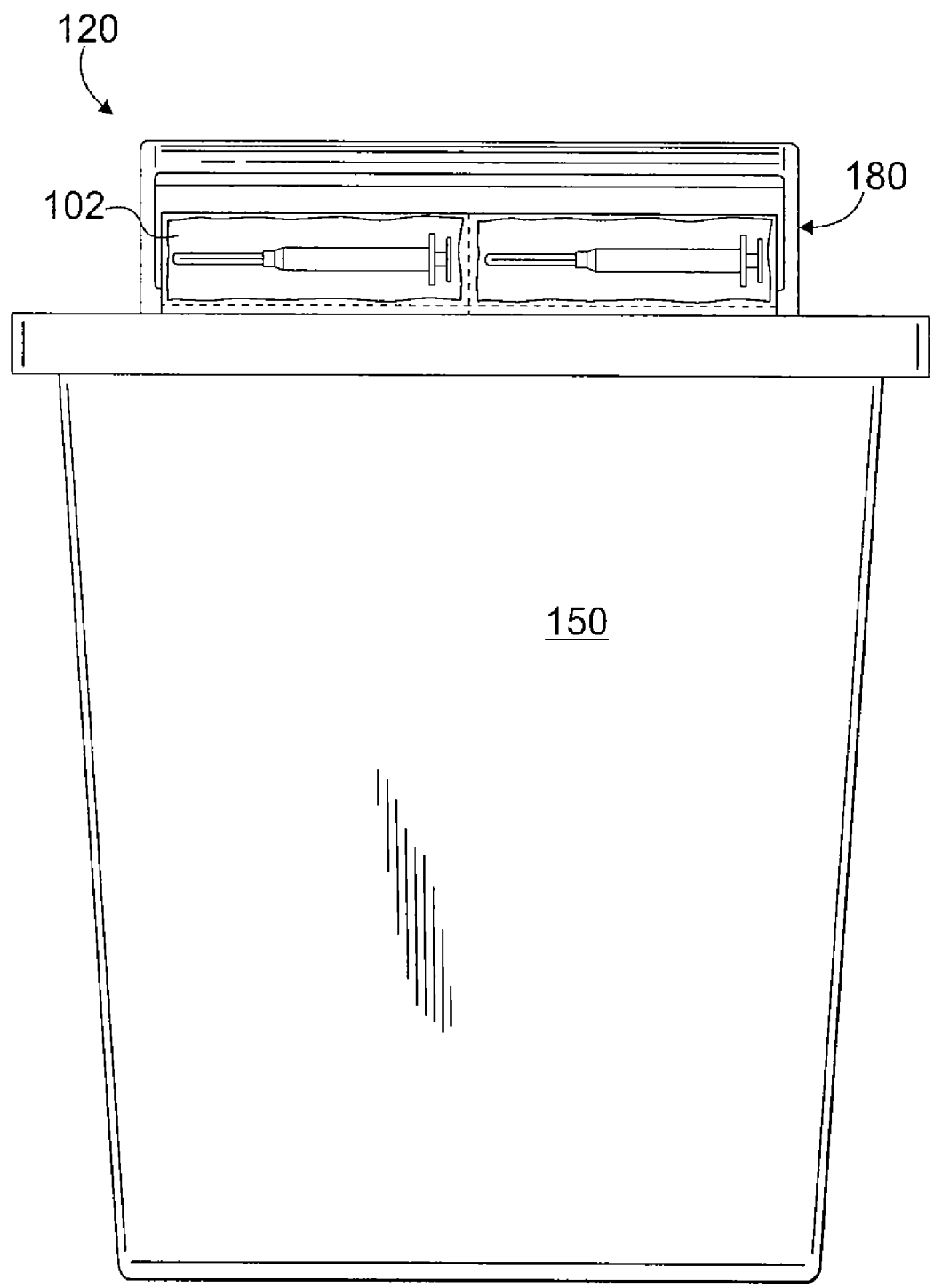
FIG. 8 is a front elevation view of a second exemplary embodiment of a sharps dispensing and disposal system in accordance with the invention.
Figure 9:
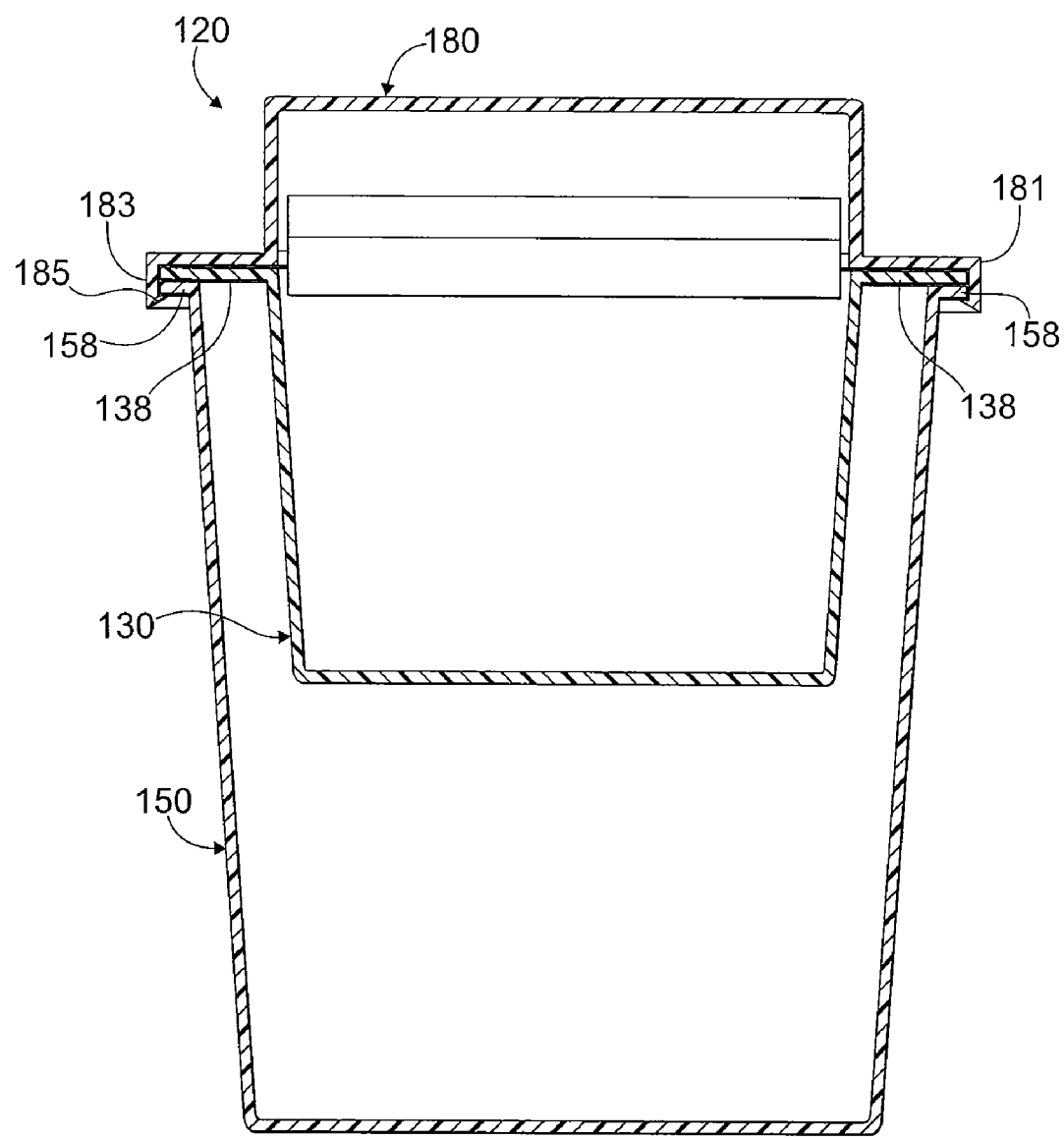
FIG. 9 is a front cross sectional view of the sharps dispensing and disposal system of FIG. 8.
Figure 10:
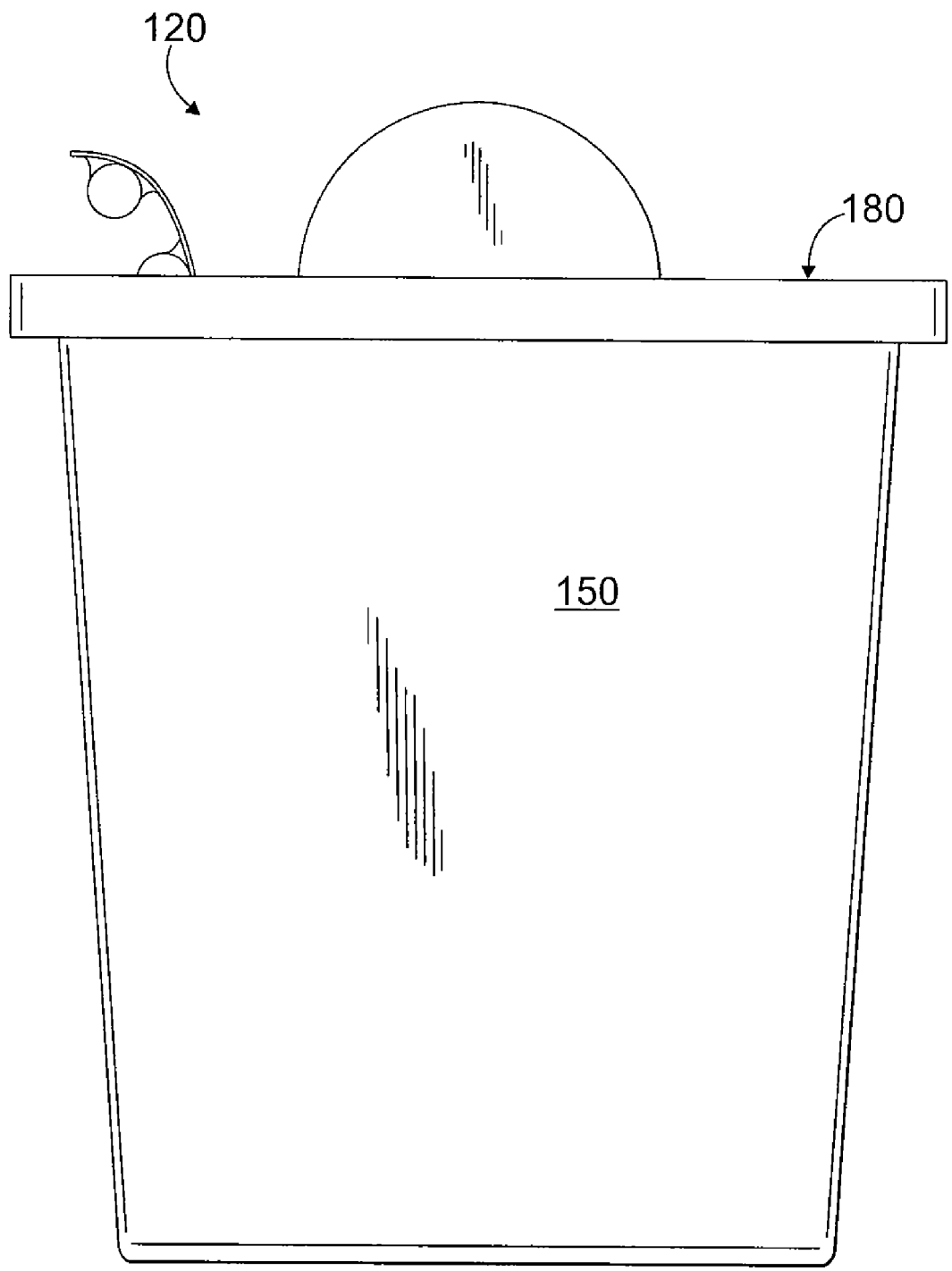
FIG. 10 is a side elevation view of the sharps dispensing and disposal system of FIG. 8.
Figure 11:
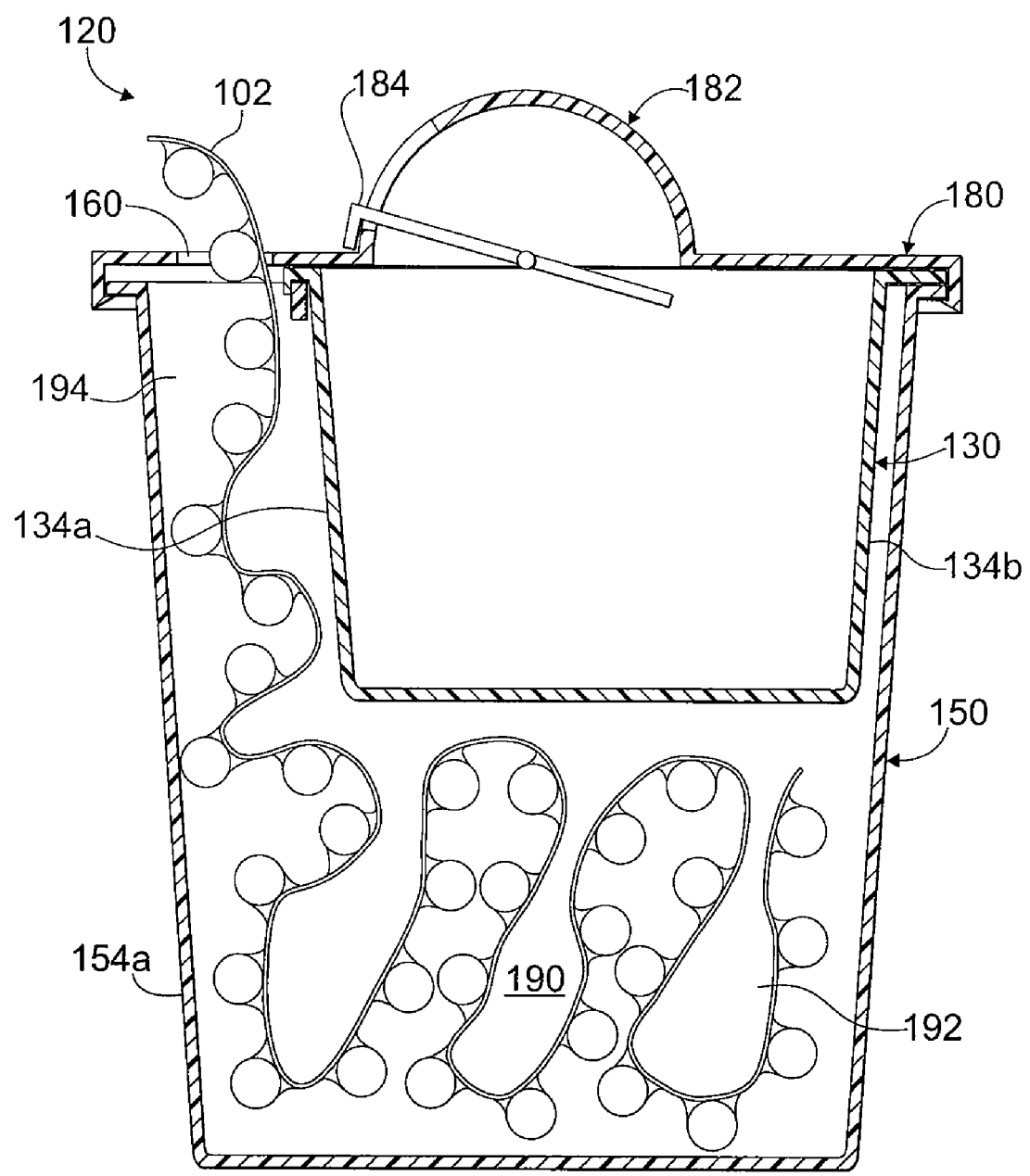
FIG. 11 is a side cross sectional view of the sharps dispensing and disposal system of FIG. 8.
Figure 12:
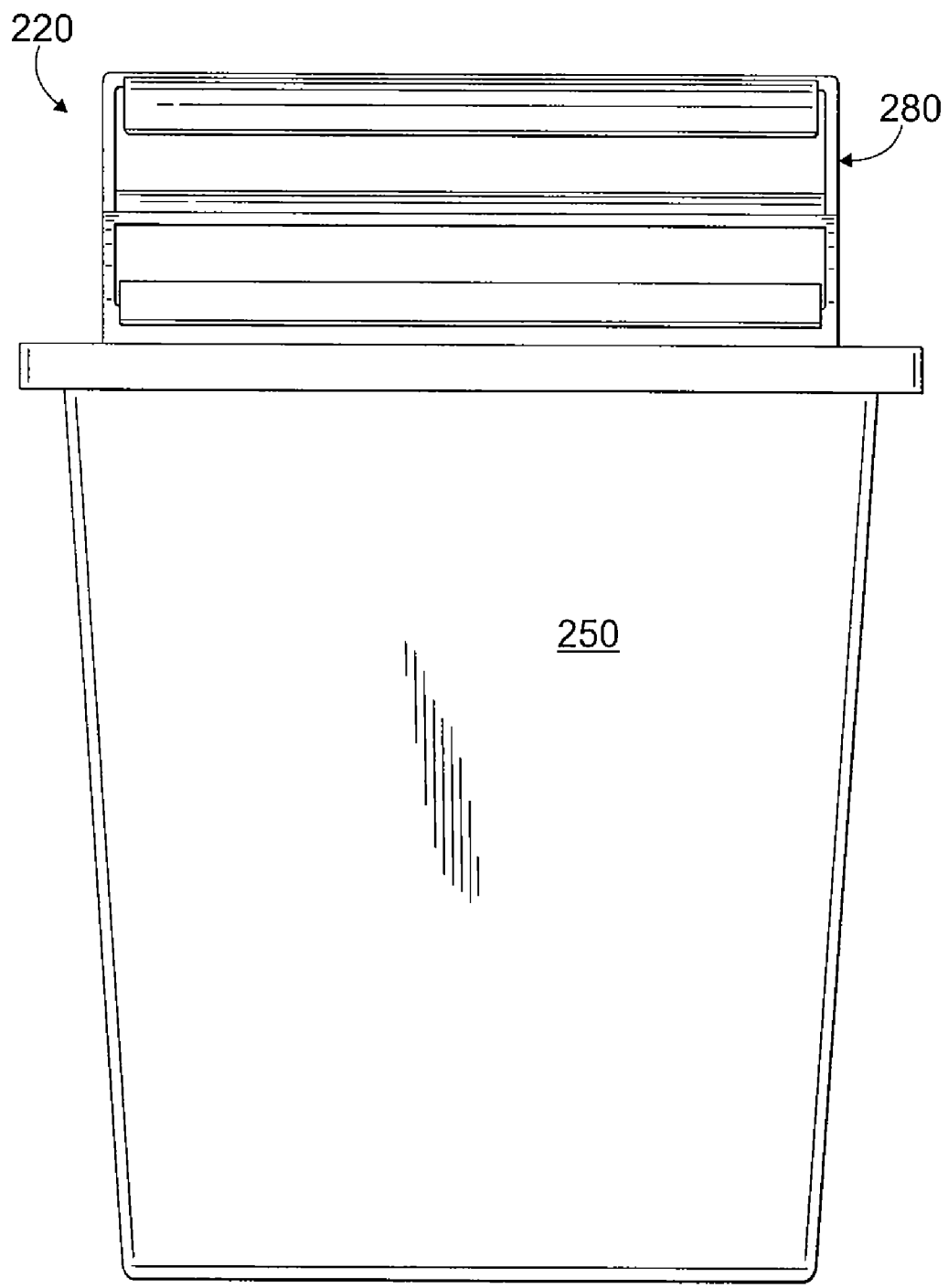
FIG. 12 is a front elevation view of a third exemplary embodiment of a sharps dispensing and disposal system in accordance with the invention.
Figure 13:
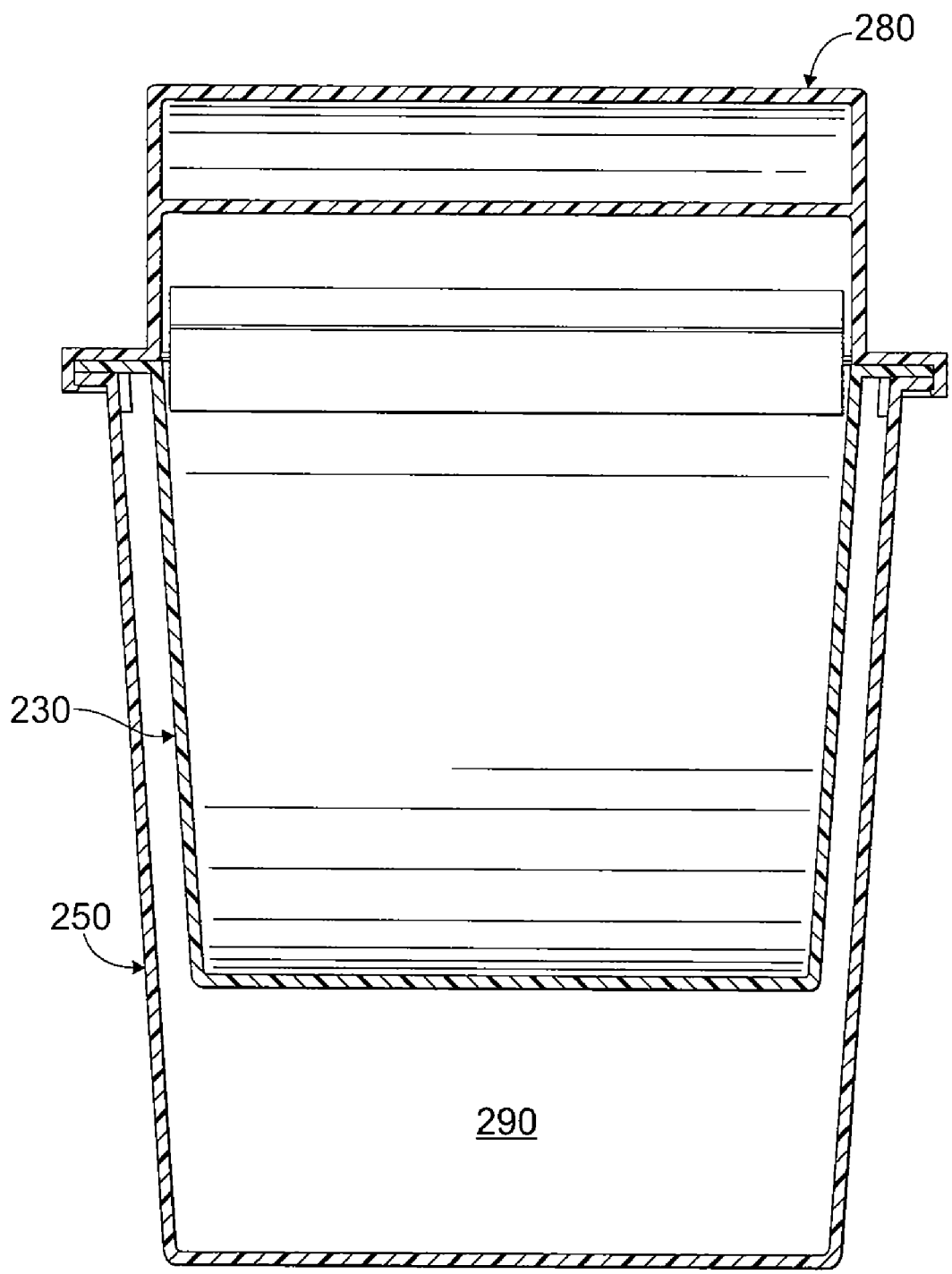
FIG. 13 is a front cross sectional view of the sharps dispensing and disposal system of FIG. 12.
Figure 14:
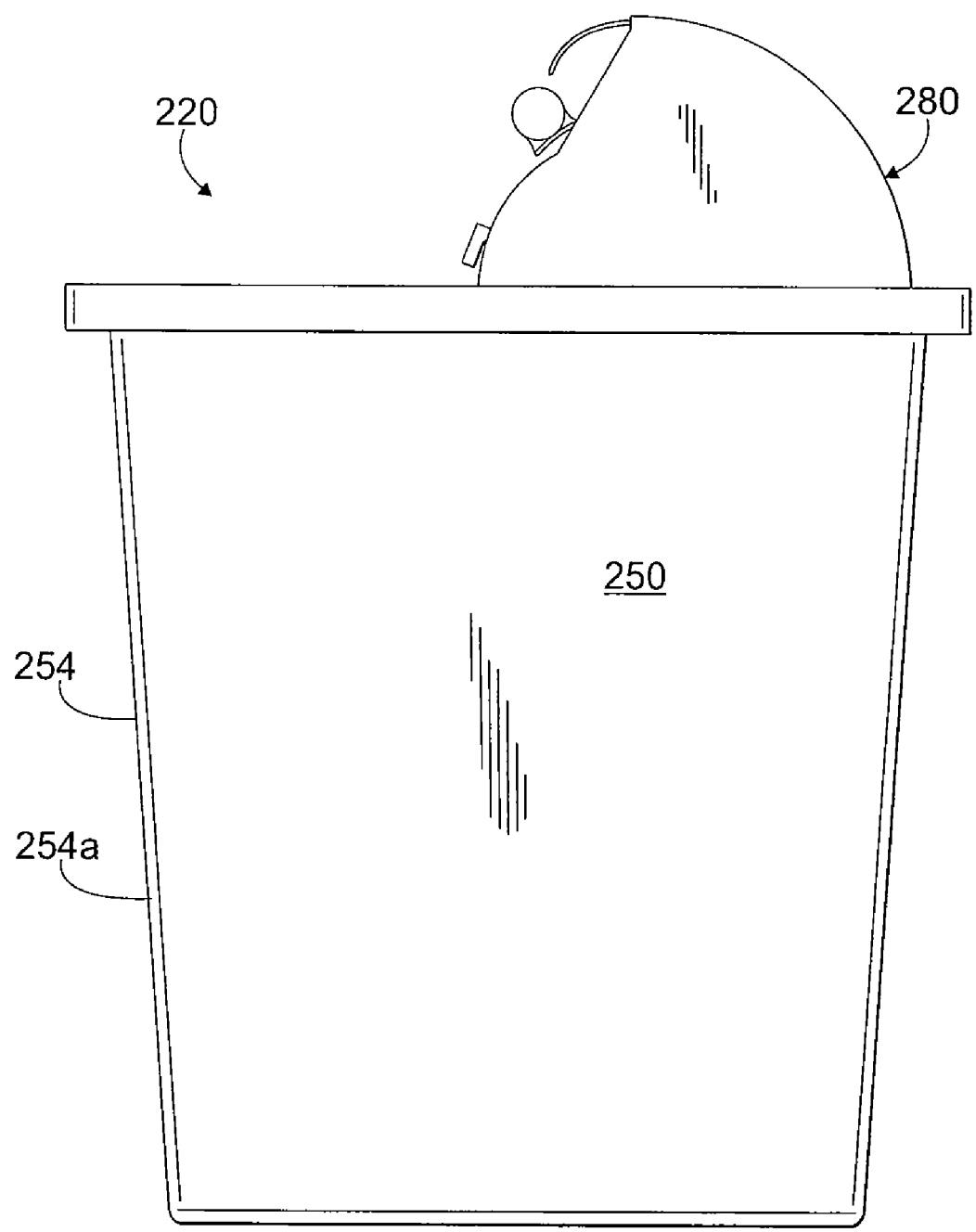
FIG. 14 is a side elevation view of the sharps dispensing and disposal system of FIG. 12.

The dimensions of disposal container 30 are smaller than corresponding dimensions of the dispensing container 50, such that a gap or chamber is formed between the containers when the containers are stacked together. Among other functions, the chamber provides a storage area for sterile sharps, and a conduit for dispensing sterile sharps from the dispensing container. A variety of configurations are possible, as will be appreciated from the embodiments described. Referring to FIG. 7, for example, disposal container 30 and dispensing container 50 form a chamber 90 that surrounds the four sidewalls and the bottom wall of the disposal container. Chamber 90 includes a storage area 92 for storing a plurality of sterile sharps 2 to be dispensed. The sterile sharps 2 are contained within a sheet of blister packages, with each blister package being surrounded by perforations that allow the packages to be individually torn from the sheet. It will be appreciated that a number of packaging options may be used with the invention. The sheet of sterile sharps 2 are arranged as a series or strip of sharps that extend around outer wall 32 of disposal container 30. The sterile sharps 2 extend through a dispensing chute 94 within chamber 90 and exit through an outlet 60 in outer wall 52. Outlet 60 may optionally include an edge 64 or tearing surface to assist in tearing each sharps package from the strip. If a tearing surface 64 is used, it is preferably formed with a blunt edge that minimizes the risk of injuring a user's finger or hand. One option is to position tearing edge 64 on the interior of dispensing container 50, where it is out of reach and less likely to contact the user during dispensing.

Disposal container 30 can be supported inside dispensing container 50 in a number of ways, including support racks or frames molded into the interior of dispensing container. A rigid support mechanism that fixes the bottom of disposal container 30 to the bottom of dispensing container 50 is possible, but not preferred over an arrangement in which the bottom of the disposal container is isolated from the walls of dispensing container. In the preferred embodiment, disposal container 30 is suspended within dispensing container 50 in a floating arrangement. The floating arrangement insulates the contents of the disposal container 30 from external forces exerted on the dispensing container 50. This reduces the potential for contaminated sharps breaking and releasing residual fluids from the contaminated sharps into the container. Disposal container 30 is preferably suspended in a position in which all four sidewalls 34 of the disposal container and bottom wall 36 are separated from the walls of the dispensing container. In such an arrangement, chamber 90 between disposal container 30 and dispensing container 50 creates a shock absorbing buffer zone around five sides of the disposal container (i.e. the four sidewalls 34 and bottom wall 36).

Figure 6:
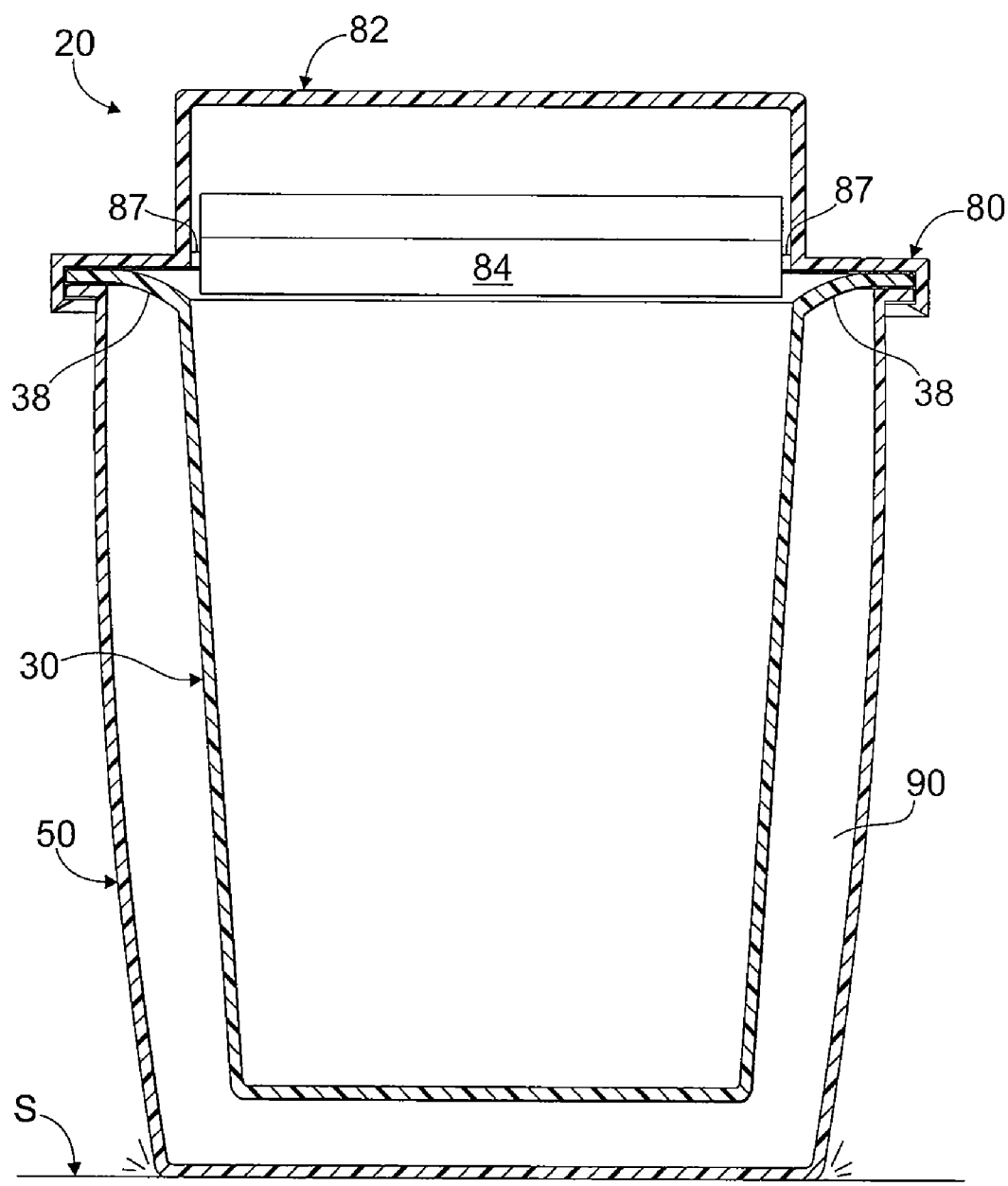
FIG. 6 is a front cross sectional view of the sharps dispensing and disposal system of FIG. 1, showing the system under a dynamic condition.

The internal suspension of disposal container 30 is provided by the flange 38 resting on shelf 58a. The thickness and width of flange 38 may be selected so as to provide a rigid support. Alternatively, flange 38 may be configured so as to provide an "elastic support member" that acts like a spring or internal shock. In this arrangement, flange 38 cushions the fall of the disposal container in the event that the container system 20 is dropped. For example, in the event that system 20 is dropped onto a flat surface with the bottom wall of dispensing container 50 hitting a hard surface, flange 38 may be constructed so as to act as a cushioning member that absorbs at least some of the shock forces. Forces that reverberate through the outer wall of dispensing container 50 may be absorbed or dampened by the cushioning effect of flange 38. This cushioning effect is schematically illustrated in FIG. 6, which shows system 20 colliding with a hard surface "S" after being dropped. In such an embodiment, the thickness "T" of flange 38, as shown in FIG. 7, would preferably be small in comparison to the width "W" so that the flange has sufficient flexibility. Flexing of flange 38 allows disposal container 30 to continue moving relative to dispensing container 50 at the point of collision. Relative motion of disposal container 30 will decelerate as the flange's range of motion is reached, at which point the resilience of flange 38 draws disposal container 30 back to its normal relaxed state. In this arrangement, the contents of disposal container 30 experience less impact and jostling, which can cause breakage of sharps or release of liquids from the sharps into the container.

In addition to cushioning the discarded sharps from external shocks, the elastic suspension of disposal container 30 inside dispensing container 50 provides a double walled container that substantially prevents or eliminates the potential for a needle puncturing through the system 20. Inner wall 32 of disposal container 30 provides a first barrier that resists against puncture. In the event that a needle penetrates into inner wall 32, the inner wall will deflect and absorb some of the penetration force, preventing the needle from penetrating further or at least reducing how far the needle penetrates through the wall. The outer wall 52 of dispensing container provides a secondary barrier in the unlikely event that a needle penetrates inner wall 32 and extends a significant distance into chamber 90.

In a preferred arrangement, the relative dimensions and placement of containers 30, 50 are such that the minimum distance $W_{min}$ between inner wall 32 and outer wall 52 is greater than the maximum needle length being discarded into container 30. For example, for a maximum needle length of 1½ inches, chamber 90 would preferably have a minimum width greater than 1½ inches. This ensures that a needle that penetrates through inner wall 32 cannot penetrate into outer wall 52 of dispensing container 50. The minimum distance between inner wall 32 and outer wall 52 can be increased beyond the maximum needle length to enhance protection of the inner container. For example, the minimum distance between inner wall 32 and outer wall 52 can be increased to 5 inches or more to create a "crumple zone", or area into which outer wall 52 can deflect without contacting inner container 32. In the event that outer wall 52 sustains an external blow and buckles inwardly, the crumple zone receives the outer wall 52 to allow the force to distribute through the outer wall but not the inner wall of disposal container 30. The dimensions of the crumple zone can vary depending on the desired volumes of the disposal and dispensing containers 30, 50, the volumetric ratio of the containers, the amount of storage area desired for sterile sharps to be dispensed, and other parameters.

System 20 is intended for use as a stationary dispensing/disposal container or a transportable handheld container. A variety of sizes are contemplated, such as a 2-quart hand held container or a 20-gallon wall-mounted container. Smaller or larger volumes may also be used, however. For smaller container systems, the dispensing container 50 may have an external geometry suitable for gripping with one hand. Moreover, dispensing container 50 may incorporate a handle portion, such as handle 57 shown in FIGS. 4 and 7.

Referring now to FIGS. 8-11, an alternate sharps dispensing and disposal system 120 is shown in accordance with the present invention. System 120 has many of the same features and components as shown and described in connection with system 20. Therefore, a number of common features found in system 120 will not be described. System 120 includes an inner disposal container 130 that is positioned inside an outer dispensing container 150, with the inner container being suspended in a position which is offset from the center of the dispensing container. Disposal container 130 is suspended by a flange 138 that overlaps a rim 158 on dispensing container 150. Flange 138 overlaps three sides of rim 158. A cover 180 is secured over the top of disposal container 130 and dispensing container 150. Cover 180 includes a resilient flexible rim 183 and tab 185 that snaps over flange 138 and rim 158 to secure the containers together.

Flange 138 extends around at least three sides of disposal container 130 and overlaps rim 158 on three sides. A front sidewall 134a of disposal container 130 is supported in abutment with or in relatively close proximity to a front side wall 154a of dispensing container 150. An opposing rear sidewall 134b is offset from a rear sidewall 154b of dispensing container 150. Sterile sharps 102 are dispensed through an outlet 160 in cover 180, as opposed to an outlet through a sidewall of dispensing container 150. This feature makes it easier to use a standard waste container for the dispensing container 150. Cover 180 includes an inlet 182 with a counterbalanced door 184 for depositing contaminated sharps into disposal container 130.

Disposal container 130 and dispensing container 150 are separated by chamber 190 that provides a protective buffer. The buffer insulates the inner disposal 130 from forces exerted on the dispensing container. Chamber 190 also provides a storage area 192 for sterile sharps to be dispensed. The space created between front sidewall 134a and front sidewall 154a forms a chute 194 for conveying sharps from sharps storage area 192 to outlet 160 in cover 180.

Referring to FIGS. 12-15, another example of a sharps dispensing and disposal system 220 is shown in accordance with the present invention. System 220 includes an inner disposal container 230 suspended within an outer dispensing container 250 in much the same manner described in the previous embodiments. A cover 280 snaps over the disposal container 230 and dispensing container 250 to secure the containers together. As before, disposal container 230 and dispensing container 250 form a chamber 290 when assembled together. Disposal container 230 includes a front sidewall 234a mounted in abutment with or in relatively close proximity to a front sidewall 254a of dispensing container 250. A rear sidewall 234b of disposal container 230 extends along a curved profile and projects through an outlet 260 formed in cover 280. To assemble system 220, disposal container 230 is placed into dispensing container 250. A flange 238 on disposal container is placed in overlapping relationship with a rim 258 on dispensing container 250, and cover 280 is snapped over the flange and the rim to secure the container together. To place cover 280 over the containers 230, 250, outlet 260 is aligned over rear sidewall 234b.

Cover 280 includes a drop inlet 282 and counterbalanced door 284 for safely depositing contaminated sharps into disposal container 250. Cover 280 also has a hood portion 282a that forms part of a dispensing chute 294. Dispensing chute 294 terminates above the drop inlet and forms an outlet opening 262 from which sharps are dispensed. In this arrangement, sterile sharps can be torn from the strip and removed from the packaging right above the drop inlet. The removed packaging can be immediately dropped into the disposal container 250, and the user can concentrate on handling the sharps without being concerned with discarding the packaging.

On one side, rear sidewall 234b provides a curved ramp that allows contaminated sharps to roll along the wall into the disposal container. On the opposite side, sidewall 234b provides a smooth surface that allows sterile sharps to be dispensed more easily. The curvature of rear sidewall 234b significantly reduces the risk of sharps becoming obstructed or caught on corners or edges inside chamber 290.

Figure 15:
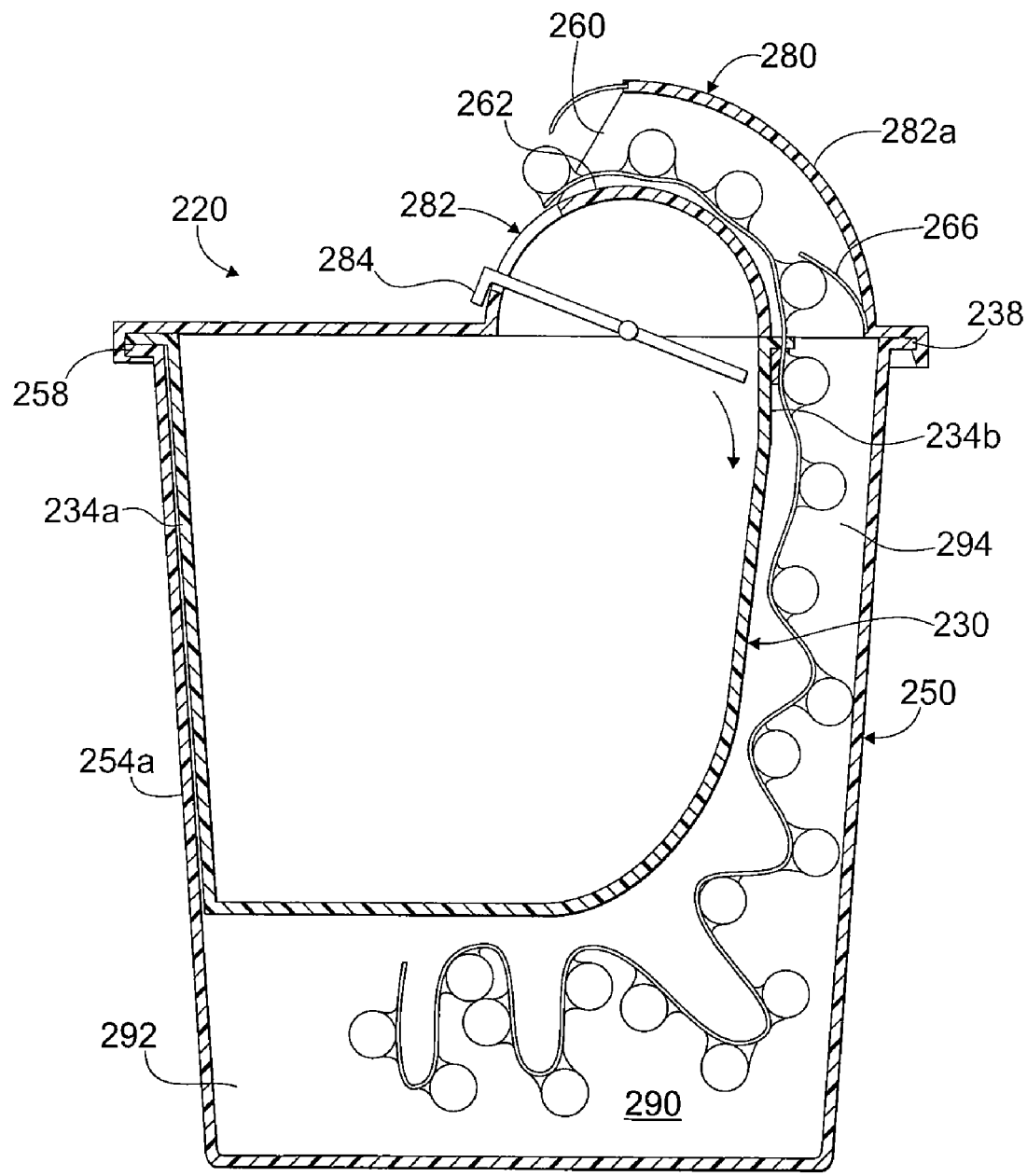
FIG. 15 is a side cross sectional view of the sharps dispensing and disposal system of FIG. 12.
Figure 16:
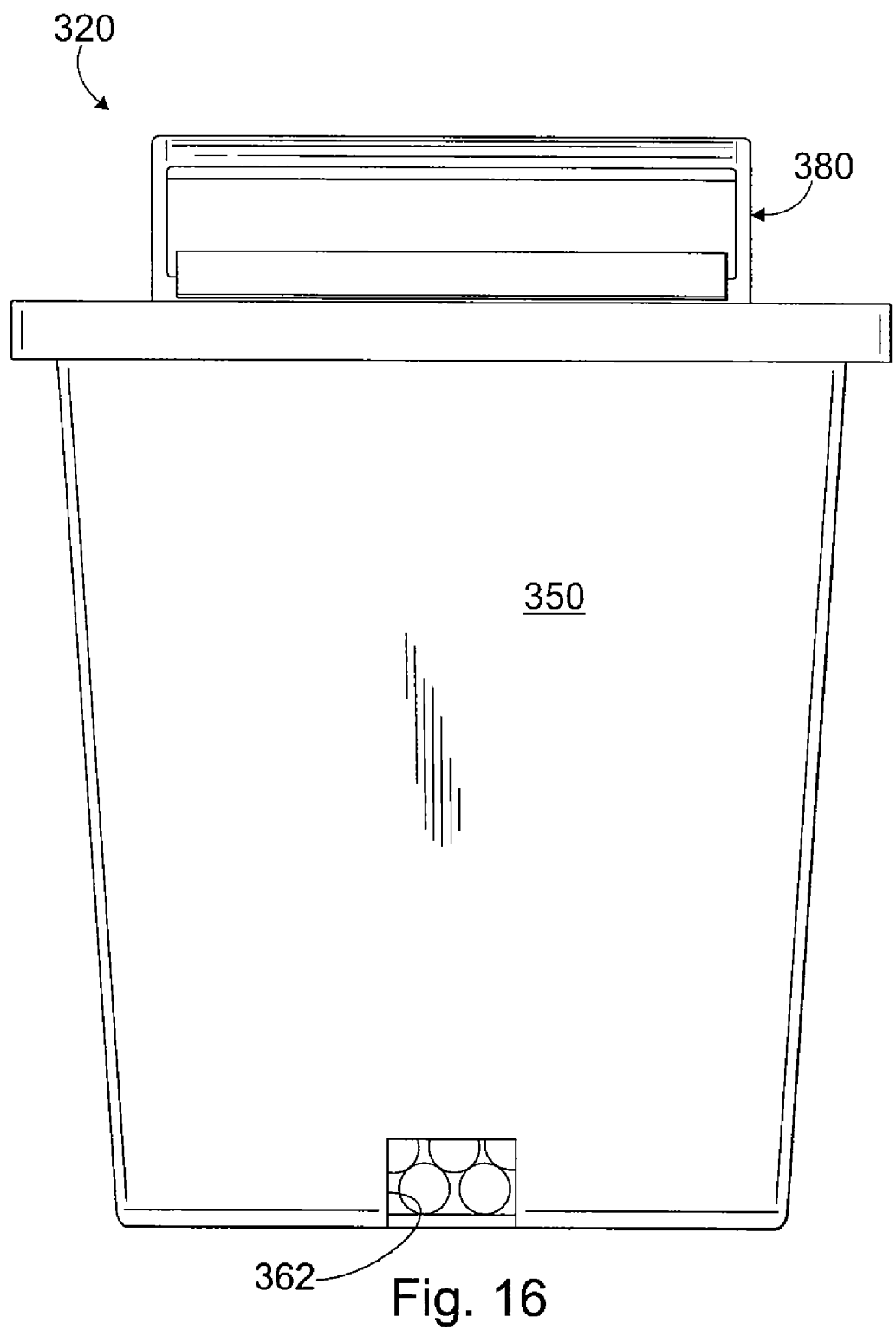
FIG. 16 is a front elevation view of a fourth exemplary embodiment of a sharps dispensing and disposal system in accordance with the invention.

Dispensing chute 294 preferably includes a mechanism to prevent sharps from slipping back into the sharps storage area 292. In FIG. 15, dispensing chute 294 includes a catch lever 266 that extends from hood portion 282a. Catch lever 266 is displaceable between a substantially open position, in which the lever is pushed against the wall of the dispensing chute, and a substantially closed position, in which the lever obstructs the dispensing chute. In the open position, lever 266 allows sharps to be pulled upwardly through the chute and out of opening 262. In the closed position, lever 266 substantially prevents sharps that are above the lever from slipping back down the chute. Lever 266 preferably includes or is attached to a biasing element that biases the lever toward the closed position. For example, lever 266 may incorporate a living hinge or other element having stored energy to urge the lever to the closed position. In this arrangement, lever 266 opens in response to sharps being pulled upwardly through the chute, and closes immediately after the sharps passes the lever to prevent the sharps from slipping back down the chute.

Referring now to FIGS. 16-19, another sharps dispensing and disposal system 320 is shown in accordance with the present invention. System 320 includes a disposal container 330 mounted in a larger dispensing container 350 that dispenses sterile sharps by gravity. A cover 380 snaps over disposal container 330 and dispensing container 350 to secure the containers together. Disposal container 330 is suspended inside dispensing container 350 by a flange 338 that is clamped to a top rim 358 of the dispensing container, as in previous embodiments. The relative dimensions of disposal container 350 and dispensing container are such that the disposal container is more or less centered within the dispensing container, with sidewalls 334 of the disposal container spaced away from sidewalls 354 of dispensing container 350.

Disposal container 330 and dispensing container 350 are separated from one another by a chamber 390 that extends around a substantial portion of the disposal container. Chamber 390 forms a sharps storage area 392 that connects with a dispensing chute 394 at the bottom of the dispensing container 350. Chamber 390 also provides a protective zone to shield the disposal container from external forces exerted on dispensing container, as well as provide a protected enclosure in the event that a contaminated needle penetrates through the inner disposal container 330.

Dispensing container 350 features a hopper-shaped bottom having a pair of opposing symmetrical ramps 351 that converge downwardly and inwardly to direct sterile sharps toward a trough 357 at the bottom center of the container. A front sidewall 354a of dispensing container 350 includes an outlet opening 362 that connects with trough 357. Outlet opening 362 is sufficiently large to allow a user to reach into trough 357 and remove a sterile sharps from dispensing container 350. As a sterile sharps is removed, other sharps in storage area 392 settle by gravity into trough 357 in proximity to outlet opening 362, so that dispensing container 350 provides a constant supply of sharps to the opening until the storage area 392 and trough are empty.

Figure 17:
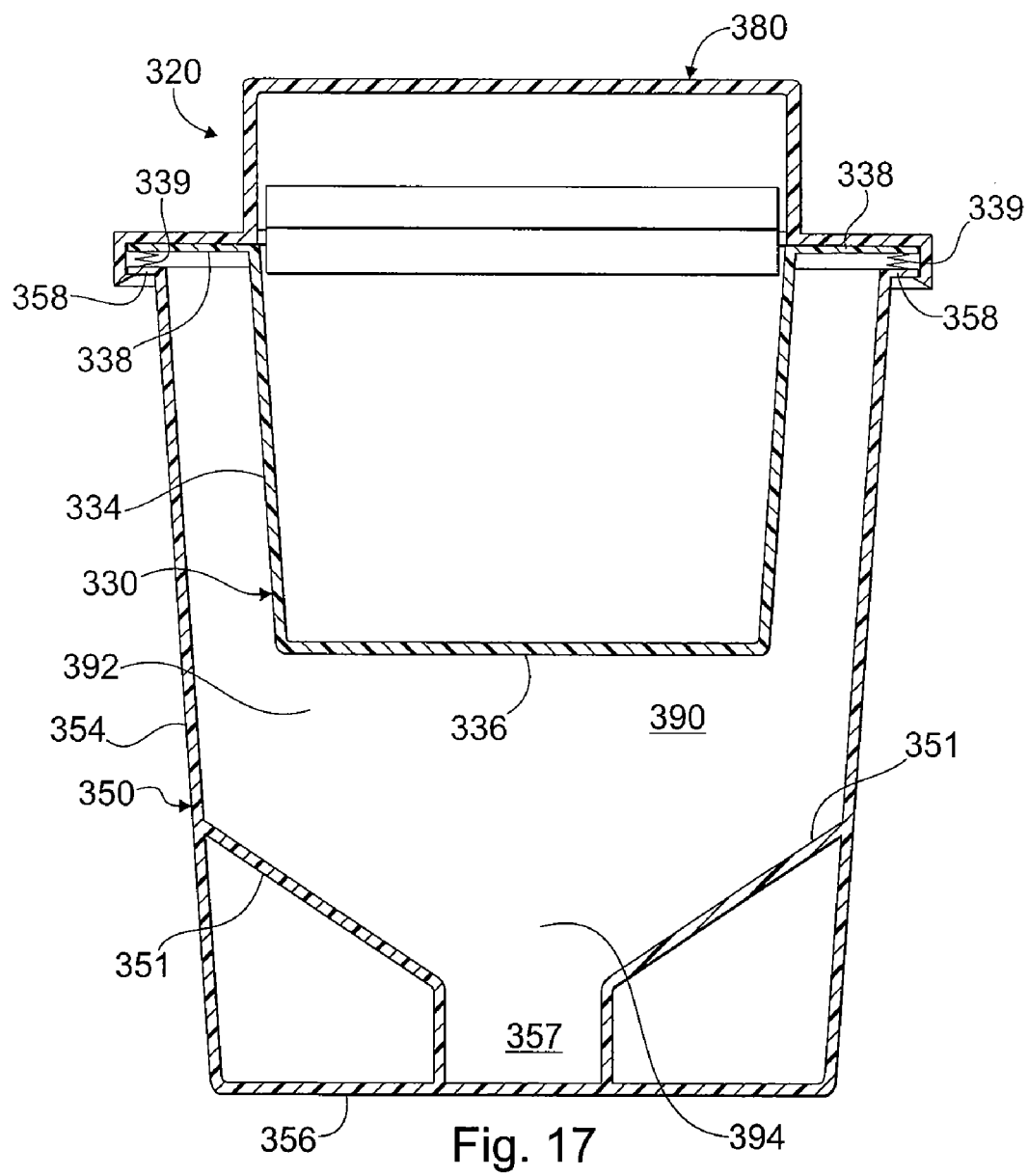
FIG. 17 is a front cross sectional view of the sharps dispensing and disposal system of FIG. 16.
Figure 18:
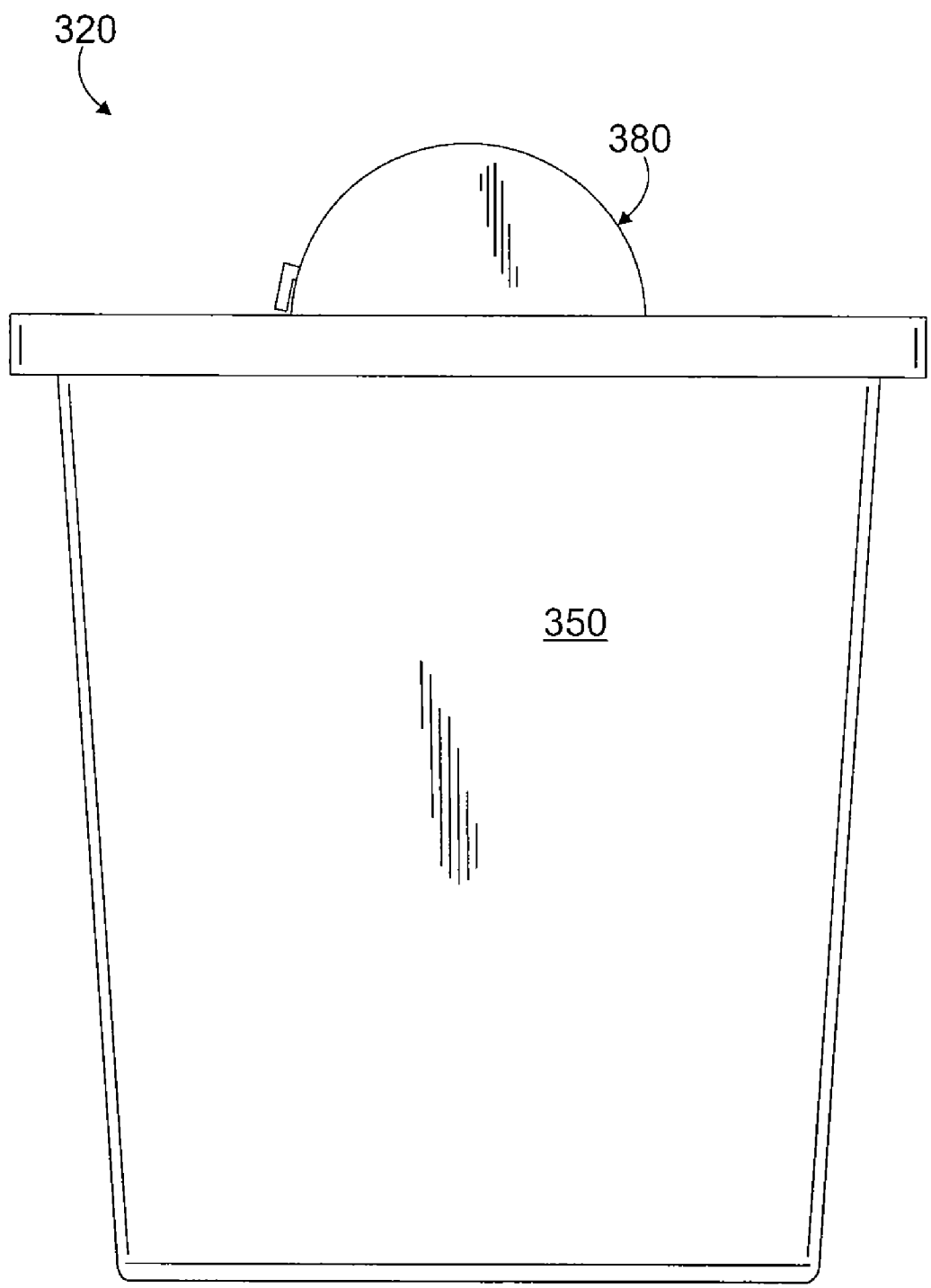
FIG. 18 is a side elevation view of the sharps dispensing and disposal system of FIG. 16.
Figure 19:
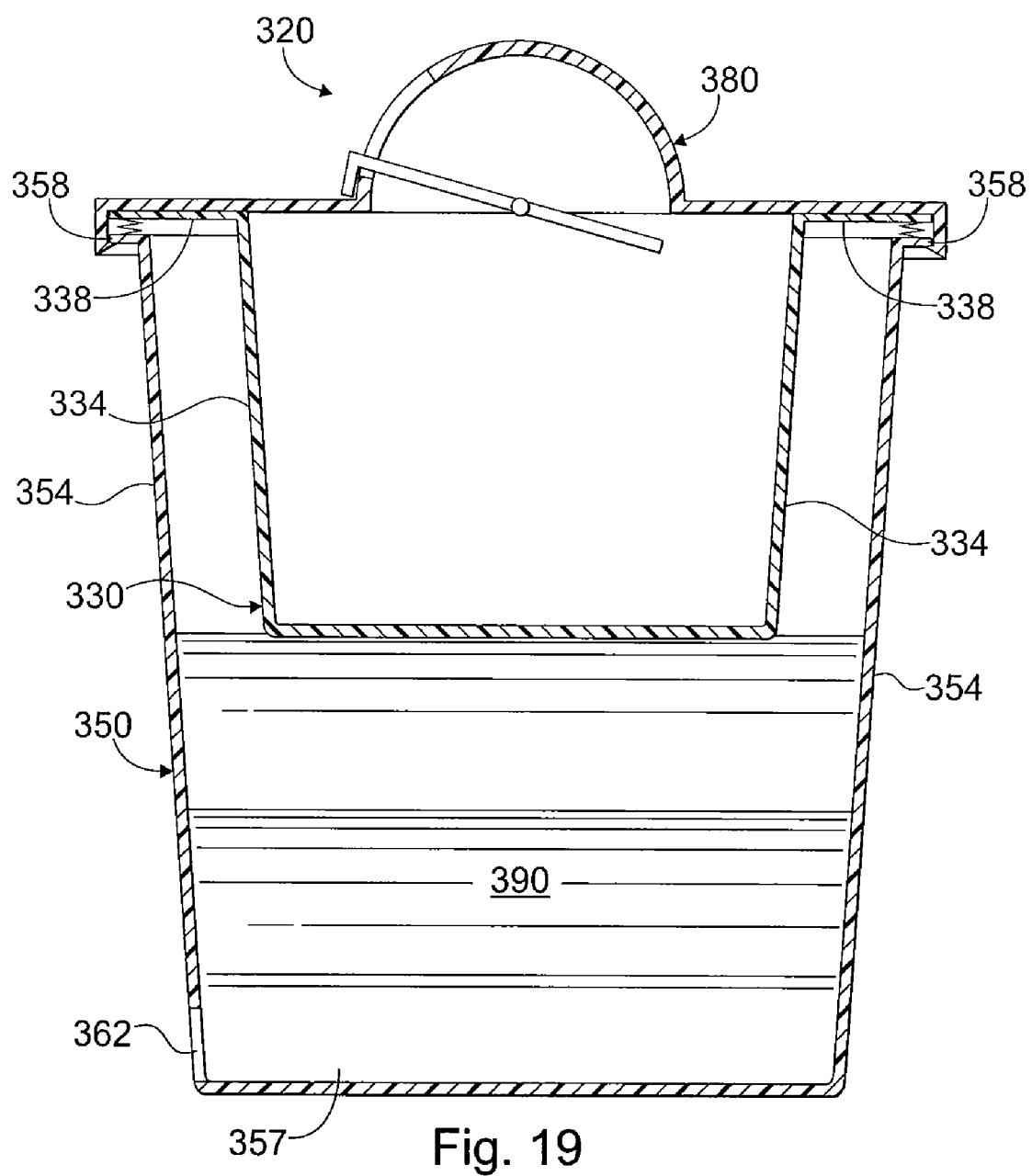
FIG. 19 is a side cross-sectional view of the sharps dispensing and disposal system of FIG. 16.
Figure 20:
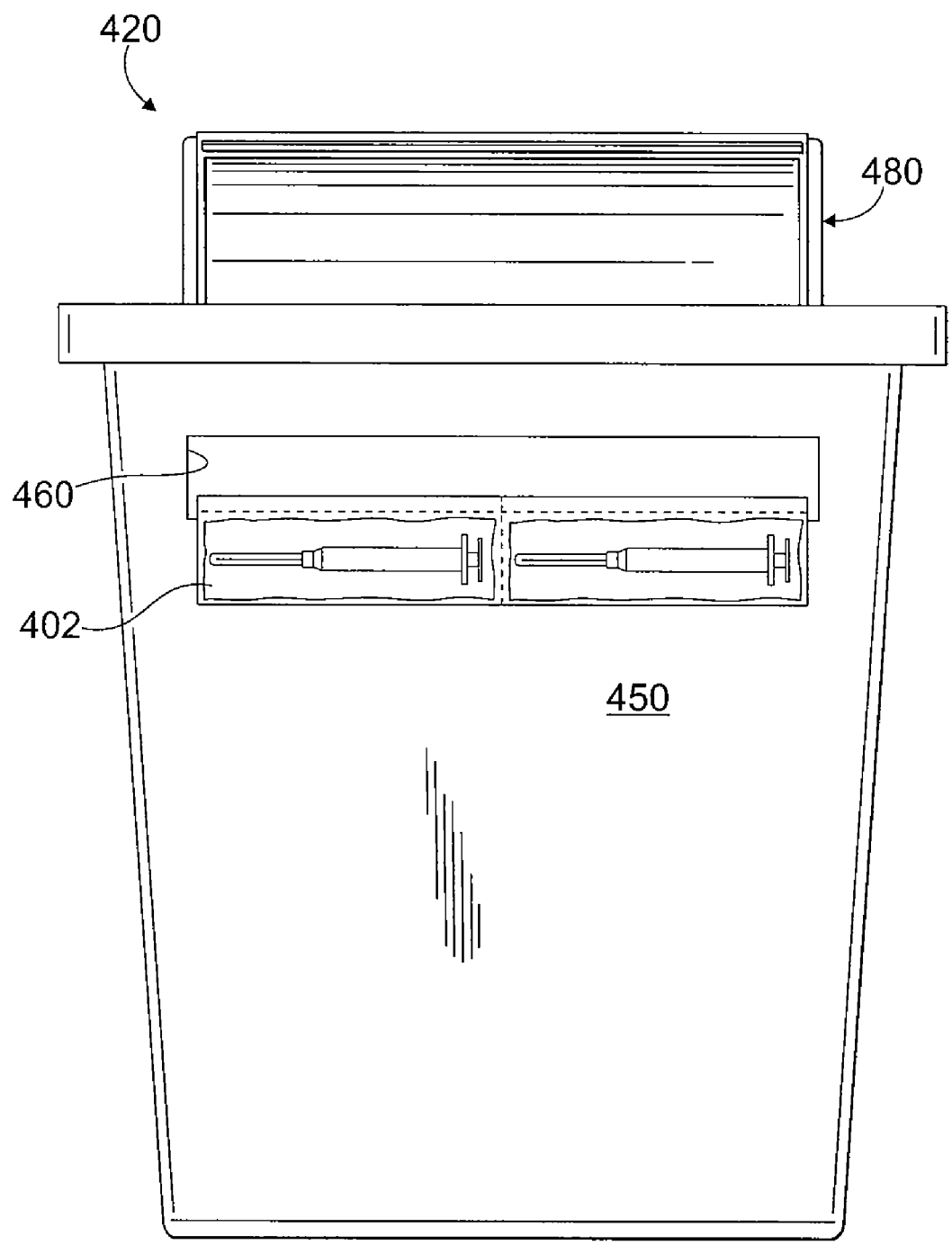
FIG. 20 is a front elevation view of a fifth exemplary embodiment of a sharps dispensing and disposal system in accordance with the invention.
Figure 21:
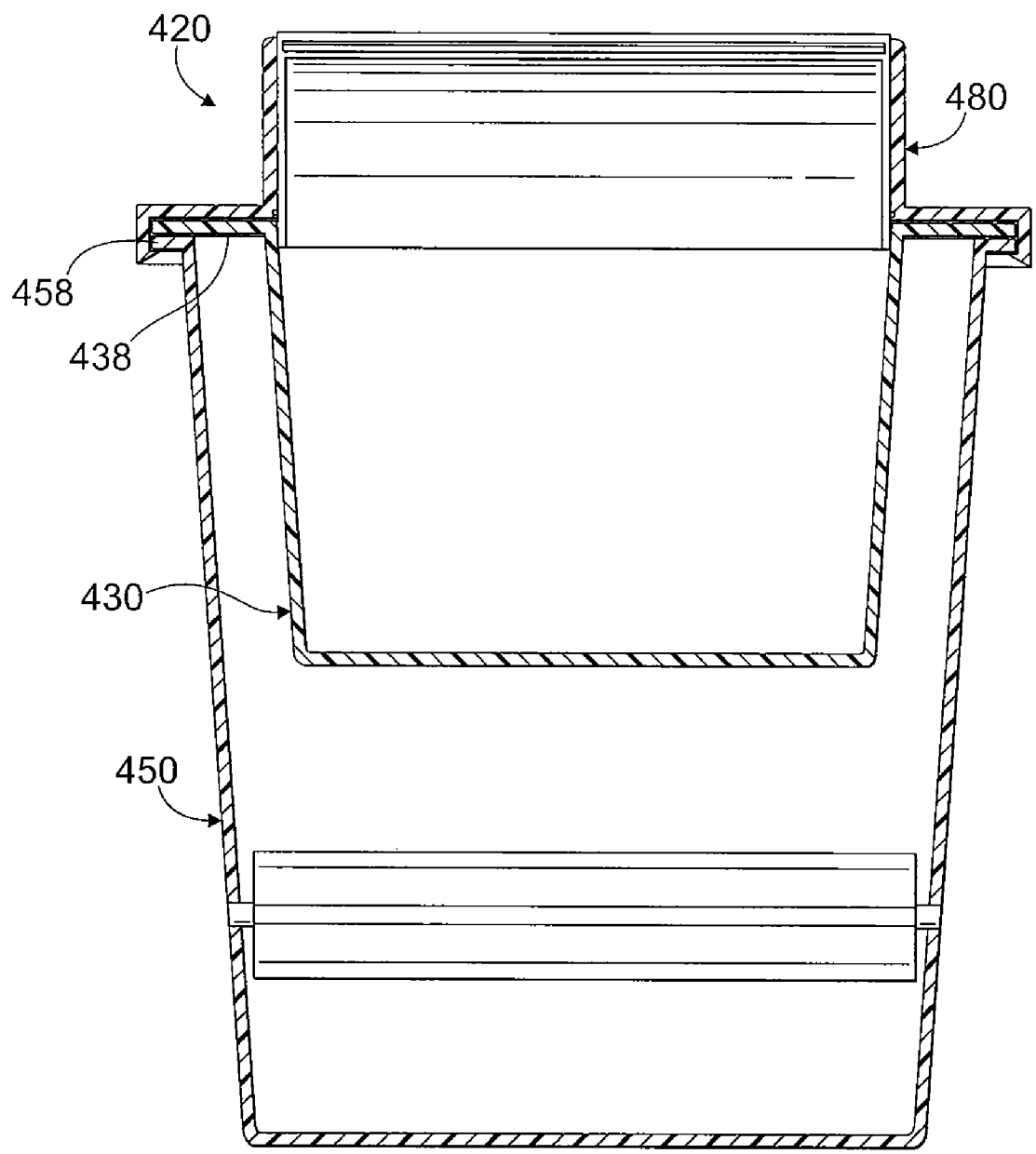
FIG. 21 is a front cross sectional view of the sharps dispensing and disposal system of FIG. 20.
Figure 22:
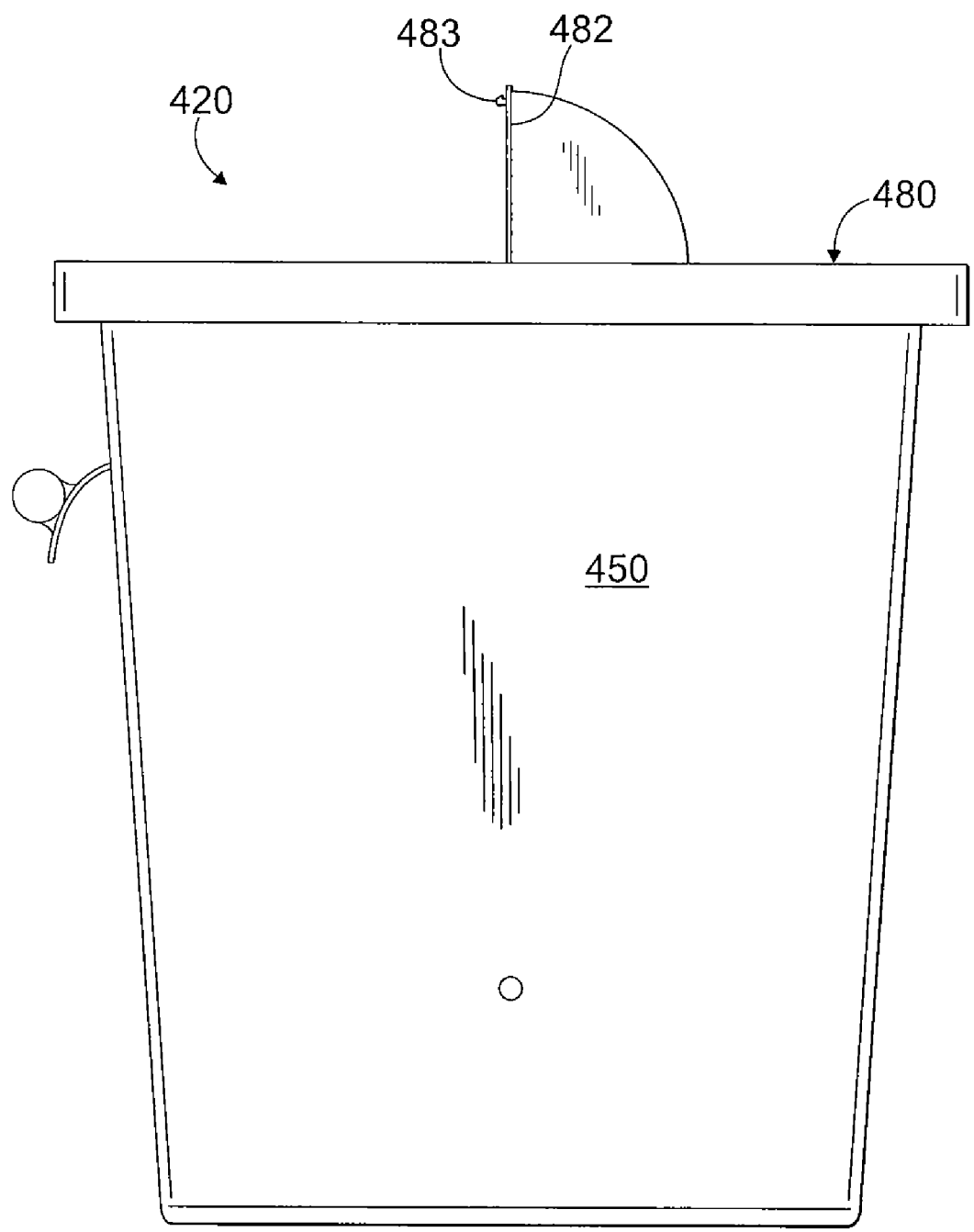
FIG. 22 is a side elevation view of the sharps dispensing and disposal system of FIG. 20.
Figure 23:
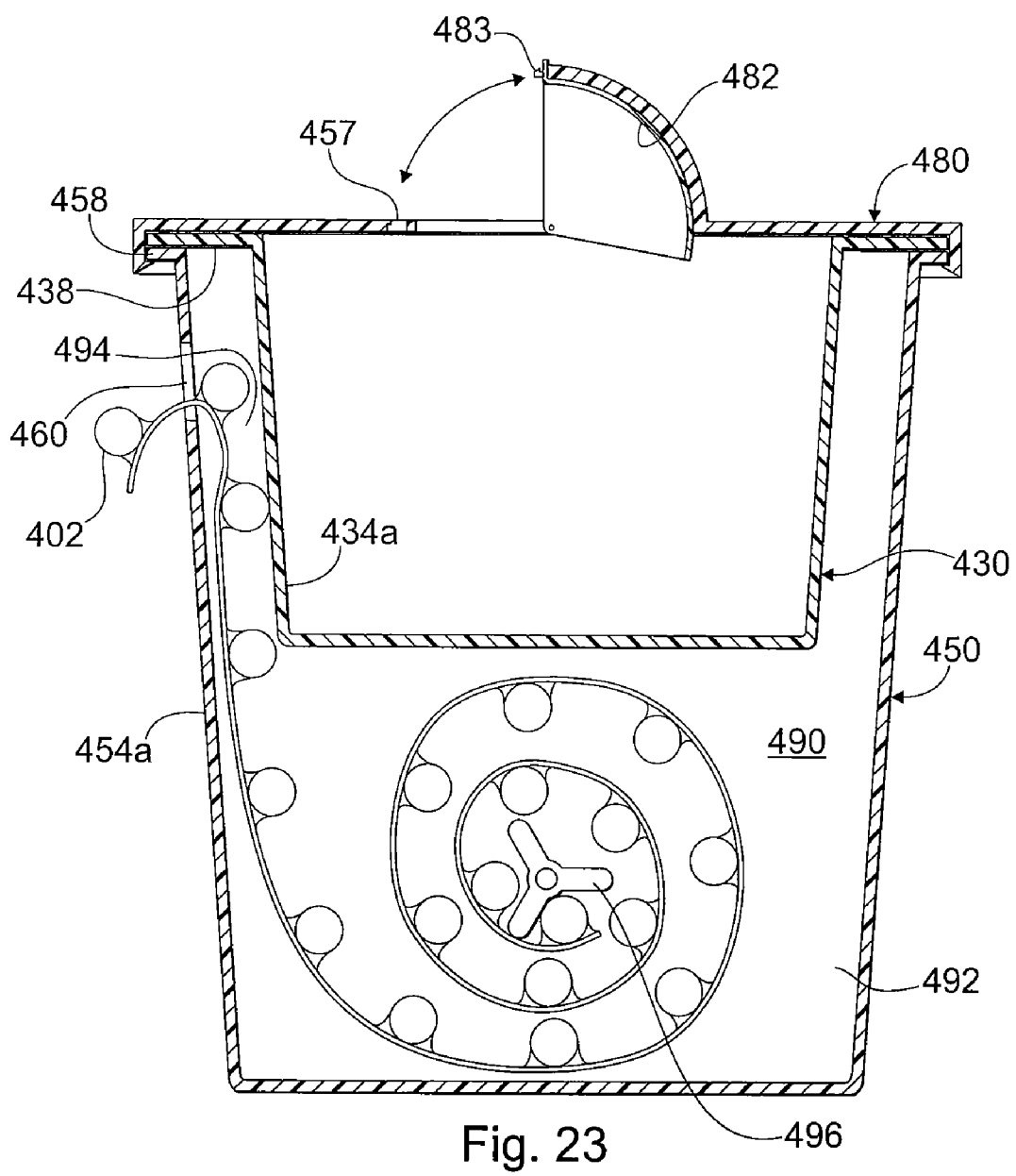
FIG. 23 is a side cross-sectional view of the sharps dispensing and disposal system of FIG. 16.

Thus far, the internal suspension or elastic support of the sharps disposal container has been described in terms of a flange supported by the rim of the sharps dispensing container. The elastic support may be provided by a number of components and mechanisms, including but not limited to one or more flexible tabs, webs, springs or other elastic elements that are either integrally formed on the sharps disposal container or are attached as separate components. Where separate components are used, the elastic elements may be formed of a flexible plastic, such as polypropylene, or a spring metal. In FIGS. 17 and 19, for example, optional compression springs 339 are shown inserted between the flange 338 and rim 358 to provide additional elastic support members.

Referring now to FIGS. 20-23, another exemplary sharps dispensing and disposal system 420 is shown in accordance with the present invention. System 420 includes a sharps disposal container 430 suspended within a sharps dispensing container 450, as in previous embodiments. A cover 480 snaps onto a flange 438 on disposal container 430 and on to a rim 458 on sharps dispensing container 450 to secure the containers together in a stacked arrangement. Flange 438, in turn, rests on a rim 458 inside dispensing container 450. Dispensing container 450 has a roll-top door 482 having a locking tab 483. Locking tab 483 snaps into a locking slot 457 on dispensing container 450 to lock the container in a closed condition for shipping and disposal.

Disposal container 430 and dispensing container 450 are separated by a protective chamber 490. Chamber 490 includes a sharps storage area 492 directly beneath disposal container 430. A rotatable spindle or roller 496 is mounted in sharps storage area 492 to support a roll of sterile sharps 402 that are packaged together in series. Chamber 490 also includes a dispensing chute 494 that extends between a front sidewall 434a of disposal container 430 and a front sidewall 454a of dispensing container 450. Front sidewall 454a of dispensing container 450 includes an outlet 460 through which sharps 402 can be dispensed.

Although the invention is illustrated and described herein with reference to specific embodiments, the invention is not intended to be limited to the details shown. Rather, various modifications may be made in the details within the scope and range of equivalents of the claims and without departing from the invention.

What is claimed is:

1. A sharps dispensing and disposal system comprising:
   a sharps disposal container having an inner wall and an inlet for depositing used sharps into the sharps disposal container; and
   a sharps dispensing container comprising an outer wall, the outer wall surrounding at least a portion of the sharps disposal container and forming a buffer zone extending between the inner wall and the outer wall, wherein the outer wall includes at least one dispensing outlet and a cutting blade adjacent the dispensing outlet.

2. The sharps dispensing and disposal system of claim 1 wherein the inner wall and the outer wall are generally trapezoidal in cross section.

3. The sharps dispensing and disposal system of claim 1 wherein the buffer zone has a first sharps storage capacity and the sharps disposal container has a second sharps storage capacity, the first sharps storage capacity being less than or equal to the second sharps storage capacity.

4. A sharps dispensing and disposal system, which comprises:

a sharps dispensing container defining an outlet;

a sharps disposal container substantially disposed within the sharps dispensing container and mounted in fixed suspended relation therewith to thereby define a chamber between the sharps disposal container and the sharps dispensing container, the sharps disposal container defining an opening for receiving contaminated sharps;

a plurality of sterile sharps disposed within the chamber for dispensing through the outlet of the sharps dispensing container;

a cover mounted with respect to the sharps disposal container, the cover including a drop inlet in communication with the opening of the sharps disposal container for depositing the contaminated sharps; and wherein the sharps dispensing container includes an outer wall and a peripheral rim depending from the outer wall and wherein the sharps disposal container includes an inner wall and a peripheral flange depending from the inner wall, the peripheral flange being supported by the peripheral rim to mount the sharps disposal container in the suspended relation within the sharp dispensing container.

5. The sharps dispensing and disposal system according to claim 4, wherein the cover includes a skirt, the skirt dimensioned to engage at least the peripheral rim of the sharps dispensing container to secure the cover relative to the sharps disposal container and the sharps dispensing container.

6. The sharps dispensing and disposal system according to claim 4 wherein the sharps dispensing container and the sharps disposal container each include a side wall and a bottom wall, the bottom walls being in spaced relation to define a lower first portion of the chamber.

7. The sharps dispensing and disposal system according to claim 6 wherein the side walls of the sharps dispensing container and the sharps disposal container are in spaced relation to define a second portion of the chamber.

8. A sharps dispensing and disposal system, which comprises:

a sharps dispensing container defining an outlet;

a sharps disposal container substantially disposed within the sharps dispensing container and mounted in fixed suspended relation therewith to thereby define a chamber between the sharps disposal container and the sharps dispensing container, the sharps disposal container defining, an opening for receiving contaminated sharps;

a plurality of sterile sharps disposed within the chamber for dispensing through the outlet of the sharps dispensing container; and wherein the sharps dispensing container includes an outer wall and a peripheral rim depending from the outer wall and wherein the sharps disposal container includes an inner wall and a peripheral flange depending from the inner wall, the peripheral flange being supported by the peripheral rim to mount the sharps disposal container in the suspended relation within the sharp dispensing container.

* * * * *